US006953778B2

(12) United States Patent
Carroll

(10) Patent No.: US 6,953,778 B2
(45) Date of Patent: Oct. 11, 2005

(54) METHODS AND COMPOSITIONS FOR THE DIAGNOSIS AND TREATMENT OF HEMATOLOGICAL DISORDERS USING 2777

(75) Inventor: Joseph M. Carroll, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 346 days.

(21) Appl. No.: 10/281,867

(22) Filed: Oct. 28, 2002

(65) Prior Publication Data

US 2003/0091571 A1 May 15, 2003

Related U.S. Application Data

(60) Provisional application No. 60/335,251, filed on Oct. 31, 2001.

(51) Int. Cl.$^7$ .................. A61K 38/00; G01N 33/53; C07K 14/00
(52) U.S. Cl. .................. 514/12; 530/350; 435/7.92
(58) Field of Search .................. 435/7.92; 514/12; 530/350

(56) References Cited

U.S. PATENT DOCUMENTS

| 5,292,652 A | 3/1994 | Dovey et al. |
| 5,424,205 A | 6/1995 | Dovey et al. |

FOREIGN PATENT DOCUMENTS

WO   WO 92/07068 A1   4/1992

OTHER PUBLICATIONS

Kato, A. et al., "Cloning, Amino Acid Sequence and Tissue Distribution of Porcine Thimet Oligopeptidase: A Comparison with Soluble Angiotensin–Binding Protein", European Journal of Biochemistry 221:159–165 (1994).
Kato, A. et al., "Targeting of Endopeptidase 24.16 to Different Subcellular Compartments by Alternative Promoter Usage", Journal of Biological Chemistry 272(24):15313–15322 (1997).
Milner, N. et al., "Selecting Effective Antisense Reagents on Combinatorial Oligonucleotide Arrays", Nature Biotechnology 15 :537–541 (1997).
Pierotti, A. et al., "Molecular Cloning and Primary Structure of Rat Testes Metalloendopeptidase EC 3.4.24.15", Biochemistry 29:10323–10329 (1990).
Thompson, A. et al., "Cloning and Functional Expression of a Metalloendopeptidase from Human Brain with the Ability to Cleave a β–APP Substrate Peptide", Biochemical and Biophysical Research Communications 213(1):66–73 (1995).
Tullai J. W. et al., "The Neuropeptide Processing Enzyme EC 3.4.24.15 is Modulated by Protein Kinase A Phosphorylation", Journal of Biological Chemistry 275 (47):36514–36522 (2000).

Hirose S., "Thimet Oligopeptidase [*Sus scrofa*]" Dec. 25, 2002 (sequence) GenBank [online] Bethesda, MD, USA: National Center for Biotechnology Information [retrieved on Oct. 21, 2003]. Retrieved from the Internet: URL: http://www.ncbi.nlm.nih.gov/>. GenBank Accession No. BAA19107.

Strausberg R., "Thimet Oligopeptidase 1 [*Homo sapiens*]" Jul. 12, 2001 (sequence) GenBank [online] Bethesda, MD, USA: National Center for Biotechnology information [retrieved on Oct. 21, 2003]. Retrieved from the Internet: URL: http://www.ncbi.nlm.nih.gov/>. GenBank Accession No. AAH00583.

Lopingco M. C., et al., "Mus Musculus Thimet Oligopeptidase mRNA, complete cds." Nov. 28, 2000 (sequence) GenBank [online] Bethesda, MD, USA: National Center for Biotechnology information [retrieved on Oct. 21, 2003]. Retrieved from the Internet: URL: http://www.ncbi.nlm.nih.gov/>. GenBank Accession No. AF314187.

Pierotti A. et al., "Rat Metalloendopeptidase mRNA, complete cds." Apr. 27, 1993 (sequence) GenBank [online] Bethesda, MD, USA: National Center for Biotechnology information [retrieved on Oct. 21, 2003]. Retrieved from the Internet: URL: http://www.ncbi.nlm.nih.gov/>. GenBank Accession No. M61142.

(Continued)

*Primary Examiner*—Robert A. Wax
*Assistant Examiner*—Suzanne M. Mayer
(74) *Attorney, Agent, or Firm*—Millennium Pharmaceuticals, Inc.

(57) ABSTRACT

The present invention relates to methods and compositions for the diagnosis and treatment of hematological disorders, including, but not limited to, apalstic anemia, hemophilia, sickle cell anemia, thalassisemia, blood loss and other blood disorders, e.g., blood diorders related to bone marrow irradiation or chemotherapy treatment or renal failure. The invention further provides methods for identifying a compound capable of treating a hematological disorder. The invention also provides methods for identifying a compound capable of modulating a hematopoietic cell activity. Yet further, the invention provides a method for modulating a hematopoietic cell activity. In addition, the invention provides a method for treating a subject having a hematological disorder characterized by aberrant 2777 polypeptide activity or aberrant 2777 nucleic acid expression. In another aspect, the invention provides methods for increasing hematopoietic cell proliferation in a subject and methods for modulating hematopoietic cell apoptosis in a subject.

15 Claims, 7 Drawing Sheets

OTHER PUBLICATIONS

Strausberg R., "*Homo sapiens* Thimet Oligopeptidase 1, mRNA (cDNA Clone MGC:8357 IMAGE:2819803), complete cds." Oct. 4, 2003 (sequence) GenBank [online] Bethesda, MD, USA: National Center for Biotechnology information [retrieved on Oct. 21, 2003]. Retrieved from the Internet: URL: http://www.ncbi.nlm.nih.gov/>. GenBank Accession No. BC002391.

Strausberg R., "*Homo sapiens* Thimet Oligopeptidase 1, mRNA (cDNA Clone MGC:10587 IMAGE:3690133), complete cds." Oct. 4, 2003 (sequence) GenBank [online] Bethesda, MD, USA: National Center for Biotechnology information [retrieved on Oct. 21, 2003]. Retrieved from the Internet: URL: http://www.ncbi.nlm.nih.gov/>. GenBank Accession No. BC013878.

Radelof U. et al., "*Homo sapiens* Chromosome 19 Sequence from PAC RPCI-1 155I10, complete sequence" Nov. 17, 2000 (sequence) GenBank [online] Bethesda, MD, USA: National Center for Biotechnology information [retrieved on Oct. 21, 2003]. Retrieved from the Internet: URL: http://www.ncbi.nlm.nih.gov/>. GenBank Accession No. AJ009611.

Dovey H. F. et al., "Sequence 6 From Patent US 5424205" Jul. 26, 1995. (sequence) GenBank [online] Bethesda, MD, USA: National Center for Biotechnology information [retrieved on Oct. 21, 2003]. Retrieved from the Internet: URL: http://www.ncbi.nlm.nih.gov/>. GenBank Accession No. I12383.

Strausberg R., "*Homo sapiens*, Thimet Oligopeptidase 1, Clone MGC:3024 IMAGE:3163074, mRNA, complete cds." Jul. 12, 2001 (sequence) GenBank [online] Bethesda, MD, USA: National Center for Biotechnology information [retrieved on Oct. 21, 2003]. Retrieved from the Internet: URL: http://www.ncbi.nlm.nih.gov/>. GenBank Accession No. BC000583.

Munroe, D. G., "Human Thimet Oligopeptidase (THOP1) mRNA, complete cds." Nov. 30, 1995 (sequence) GenBank [online] Bethesda, MD, USA: National Center for Biotechnology information [retrieved on Oct. 21, 2003]. Retrieved from the Internet: URL: http://www.ncbi.nlm.nih.gov/>. GenBank Accession No. U29366.

Malherbe P. et al., "*H. sapiens* mRNA for Thimet Oligopeptidase (metalloproteinase)" Oct. 18, 1995 (sequence) GenBank [online] Bethesda, MD, USA: National Center for Biotechnology information [retrieved on Oct. 21, 2003]. Retrieved from the Internet: URL: http://www.ncbi.nlm.nih.gov/>. GenBank Accession No. Z50115.

Lamerdin J. E., "*Homo sapiens* Chromosome 19, BAC 41195 (CIT-B-31c16), complete sequence" Feb. 7, 1999 (sequence) GenBank [online] Bethesda, MD, USA: National Center for Biotechnology information [retrieved on Oct. 21, 2003]. Retrieved from the Internet: URL: http://www.ncbi.nlm.nih.gov/>. GenBank Accession No. AC006538.

```
Input file Fbh2777FL1.seq; Output File 2777.trans
Sequence length 2515

GAATTCCGGGGCATGCTGTGGCGGCGGTTGGGCCGAGCCAGGCCGCCTCAGTGGCCGAGGTGGCTTGGACGCGTACGAG
                                                    M   K   P   P   A   A   C        7
GTGGAACGAGGGAGGCAGCCCCAGGCGCAGACCCACAGACCACCCGCC ATG AAC CCC CCC GCA GCC TGT       21

A   G   D   M   A   D   A   A   S   P   C   S   V   V   N   D   L   R   W   D     27
GCA GGA GAC ATG GCG GAC GCA GCA TCT CCG TGC TCT GTG GTA AAC GAC CTG CGG TGG GAC    81

L   S   A   Q   Q   I   E   E   R   T   R   E   L   I   E   Q   T   K   R   V     47
CTG AGT GCC CAG CAG ATA GAG GAG CGC ACC AGG GAG CTC ATC GAG CAG ACC AAG CGC GTG   141

Y   D   Q   V   G   T   Q   E   F   E   D   V   S   Y   E   S   T   L   K   A     67
TAT GAC CAG GTT GGC ACC CAG GAG TTT GAG GAC GTG TCC TAC GAG AGC ACG CTC AAG GCG   201

L   A   D   V   E   V   T   Y   T   V   Q   R   N   I   L   D   F   P   Q   H     87
CTG GCC GAT GTG GAG GTC ACC TAC ACA GTT CAG AGG AAT ATC CTT GAC TTC CCC CAG CAT   261

V   S   P   S   K   D   I   R   T   A   S   T   E   A   D   K   K   L   S   E    107
GTT TCC CCC TCC AAG GAC ATC CGG ACA GCC AGC ACA GAG GCC GAC AAG AAC CTC TCT GAG   321

F   D   V   E   M   S   M   R   E   D   V   Y   Q   R   I   V   W   L   Q   E    127
TTC GAC GTG GAG ATG AGC ATG AGG GAG GAC GTG TAC CAG AGG ATC GTG TGG CTC CAG GAG   381

K   V   Q   K   D   S   L   R   P   E   A   A   R   Y   L   E   R   L   I   K    147
AAA GTT CAG AAG GAC TCA CTG AGG CCC GAG GCT GCG CGG TAC CTG GAG CGG CTA ATC AAG   441

L   G   R   R   N   G   L   H   L   P   R   E   T   Q   E   N   I   K   R   I    167
CTG GGC CGG AGA AAT GGG CTT CAC CTC CCC AGA GAG ACT CAG GAA AAC ATC AAA CGC ATC   501

K   K   K   L   S   L   L   C   I   D   F   N   K   N   L   N   E   D   T   T    187
AAG AAG AAG CTG AGC CTT CTG TGC ATC GAC TTC AAC AAG AAC CTG AAC GAG GAC ACG ACC   561

F   L   P   F   T   L   Q   E   L   G   G   L   P   E   D   F   L   N   S   L    207
TTC CTG CCC TTC ACG CTC CAG GAG CTA GGA GGG CTC CCC GAG GAC TTT CTG AAC TCC CTG   621

E   K   M   E   D   G   K   L   K   V   T   L   K   Y   P   H   Y   F   P   L    227
GAG AAG ATG GAG GAC GGC AAG TTG AAG GTC ACC CTC AAG TAC CCC CAT TAC TTC CCC CTC   681

L   K   K   C   H   V   P   E   T   R   R   K   V   E   E   A   F   N   C   R    247
CTG AAG AAA TGC CAC GTG CCT GAG ACC AGG AGG AAA GTG GAG GAG GCC TTC AAC TGC CGG   741

C   K   E   E   N   C   A   I   L   K   E   L   V   T   L   R   A   Q   K   S    267
TGC AAG GAG GAG AAC TGC GCT ATC CTC AAG GAG CTG GTC ACG CTG CGG GCC CAG AAG TCC   801

R   L   L   G   F   H   T   H   A   D   Y   V   L   E   M   N   M   A   K   T    287
CGC CTG CTG GGG TTC CAC ACG CAC GCC GAC TAT GTC CTG GAG ATG AAC ATG GCC AAG ACC   861

S   Q   T   V   A   T   F   L   D   E   L   A   Q   K   L   K   P   L   G   E    307
AGC CAG ACC GTG GCC ACC TTC CTA GAT GAG CTG GCG CAG AAG CTG AAG CCC CTG GGG GAG   921

Q   E   R   A   V   I   L   E   L   K   R   A   E   C   E   R   R   G   L   P    327
CAG GAG CGT GCG GTG ATT CTG GAG CTG AAG CGT GCG GAG TGC GAG CGC CGG GGC CTG CCC   981

F   D   G   R   I   R   A   W   D   M   R   Y   Y   M   N   Q   V   E   E   T    347
TTC GAC GGC CGC ATC CGT GCC TGG GAC ATG CGC TAC TAC ATG AAC CAG GTG GAG GAG ACG  1041

R   Y   C   V   D   Q   N   L   L   K   E   Y   F   P   V   Q   V   V   T   H    367
CGC TAC TGC GTG GAC CAG AAC CTG CTC AAG GAG TAC TTC CCC GTG CAG GTG GTC ACG CAC  1101

G   L   L   G   I   Y   Q   E   L   L   G   L   A   F   H   H   E   E   G   A    387
GGG CTG CTG GGC ATC TAC CAG GAG CTC CTG GGG CTG GCC TTC CAC CAC GAG GAG GGC GCC  1161

S   A   W   H   E   D   V   R   L   Y   T   A   R   D   A   A   S   G   E   V    407
AGT GCC TGG CAT GAG GAC GTG CGG CTC TAC ACC GCG AGG GAC GCG GCC TCG GGG GAG GTG  1221

V   G   K   F   Y   L   D   L   Y   P   R   E   G   K   Y   G   H   A   A   C    427
GTC GGC AAG TTC TAC CTG GAC CTG TAC CCG CGG GAA GGA AAG TAC GGG CAC GCG GCC TGC  1281

F   G   L   Q   P   G   C   L   R   Q   D   G   S   R   Q   I   A   I   A   A    447
TTT GGC CTG CAG CCC GGC TGC CTG CGG CAG GAT GGG AGC CGC CAG ATC GCC ATC GCG GCC  1341

M   V   A   N   F   T   K   P   T   A   D   A   P   S   L   L   Q   H   D   E    467
ATG GTG GCC AAC TTC ACC AAG CCC ACA GCC GAC GCG CCC TCG CTG CTG CAG CAT GAC GAG  1401

V   E   T   Y   F   H   E   F   G   H   V   M   H   Q   L   C   S   Q   A   E    487
GTG GAG ACC TAC TTC CAT GAG TTT GGC CAC GTG ATG CAC CAG CTC TGC TCC CAG GCG GAG  1461

```
                                                                              1521
TTC GCC ATG TTC AGC GGG ACC CAC GTG GAG CGG GAC TTT GTG GAG GCG CCG TCG CAG ATG
 L   E   N   W   V   W   E   Q   E   P   L   L   R   M   S   R   H   Y   R   T    527
CTG GAG AAC TGG GTG TGG GAG CAG GAG CCC CTG CTG CGG ATG TCG CGG CAC TAC CGC ACA   1581
 G   S   A   V   P   R   E   L   L   E   K   L   I   E   S   R   Q   A   N   T    547
GGC AGC GCC GTG CCC CGG GAG CTC CTG GAG AAG CTC ATT GAG TCC CGG CAG GCC AAC ACA   1641
 G   L   F   N   L   R   Q   I   V   L   A   K   V   D   Q   A   L   H   T   Q    567
GGC CTC TTC AAC CTC CGC CAG ATC GTC CTC GCC AAG GTG GAC CAG GCC CTG CAC ACG CAG   1701
 T   D   A   D   P   A   E   E   Y   A   R   L   C   Q   E   I   L   G   V   P    587
ACG GAC GCA GAC CCC GCC GAG GAC TAT GCG CGG CTC TGC CAG GAG ATC CTC GGG GTC CCG   1761
 A   T   P   G   T   N   M   P   A   T   F   G   H   L   A   G   G   Y   D   A    607
GCC ACG CCA GGA ACC AAC ATG CCT GCA ACC TTC GGC CAT CTG GCA GGT GGC TAC GAC GCC   1821
 Q   Y   Y   G   Y   L   W   S   E   V   Y   S   M   D   M   F   H   T   R   F    627
CAG TAC TAC GGG TAC CTG TGG AGC GAG GTG TAT TCC ATG GAC ATG TTC CAC ACG CGC TTC   1881
 K   Q   E   G   V   L   N   S   K   V   G   M   D   Y   R   S   C   I   L   R    647
AAG CAG GAG GGT GTC CTG AAC AGC AAG GTT GGC ATG GAT TAC AGA AGC TGC ATC CTG AGA   1941
 P   G   G   S   E   D   A   S   A   M   L   R   R   F   L   G   R   D   P   K    667
CCC GGC GGT TCC GAG GAT GCC AGC GCC ATG CTG AGG CGC TTC CTG GGC CGT GAC CCC AAG   2001
 Q   D   A   F   L   L   S   K   G   L   Q   V   A   G   C   E   P   E   P   Q    687
CAG GAC GCC TTC CTC CTG AGC AAG GGG CTG CAG GTC GCG GGC TGC GAG CCC GAG CCG CAG   2061
 V   C   *                                                                         690
GTC TGC TGA                                                                       2070
GGCCTGGCACTGCGACTGCCCAGTCTGGCCTGCGCTCCCGCCGCCCTGGTGCCTTAGCCCCGGCACAGGATGGGGCAA
GCTCTGCCACAGTGCCTTGGGACTGGACTGGCAGGGTGGCTGAGCGGCTGTCTTGCCTCTTGTCATTGTCTGTCCCCAC
CCGGTCGTGGCCCACCCGGCTAGACGGCGTCCTCAAGGCATCTGGAGGGCTTTCGTCGCTGCCAGGGCCTGGTCTTTGT
TGCACTAACACGTCTCCTCTCTGGGAAACGTCCCTTCTCAGGAGACGGCTCTTCTTTGAAATGAGGTCATTAAAAGGAA
AC
```

METHODS AND COMPOSITIONS FOR THE DIAGNOSIS AND TREATMENT OF HEMATOLOGICAL DISORDERS USING 2777

This application claims priority to U.S. provisional application No. 60/335,251, filed Oct. 31, 2001, the entire contents of which are incorporated herein by reference.

BACKGROUND OF THE INVENTION

Hematological disorders are blood associated disorders. Blood is a highly specialized tissue which carries oxygen and nutrients to all parts of the body and waste products back to the lungs, kidneys and liver for disposal. Thus, blood maintains communication between different parts of the body. Blood is also an essential part of the immune system, crucial to fluid and temperature balance, a hydraulic fluid for certain functions and a highway for hormonal messages.

All blood cells in adults are produced in the bone marrow. Red cells, white cells and platelets are produced in the marrow of bones, especially the vertebrae, ribs, hips, skull and sternum. These essential blood cells fight infection, carry oxygen and help control bleeding. Specifically, red blood cells are disc-shaped cells containing hemoglobin, which enables these cells to pick up and deliver oxygen to all parts of the body. White blood cells are the body's primary defense against infection. They can move out of the blood stream and reach tissues being invaded. Platelets are small blood cells that control bleeding by forming clusters to plug small holes in blood vessels and assist in the clotting process.

Each day the bone marrow generates and releases into the circulation several billion fully-differentiated, functional blood cells. Hematopoiesis is the process by which blood cells develop and differentiate from pluripotent stem cells in the bone marrow. Production of these cells derives from a small stock of quiescent progenitor cells (including the most primitive stem cells and other less primitive but still immature progenitors). The most primitive stem cells have the capacity to generate several billion cells containing all blood lineages. The production of such a large number of cells is achieved by extensive proliferation coupled with successive differentiation steps leading to a balanced production of mature cells.

The production of mature blood cells by the hematopoietic system involves complex interactions between soluble factors, the marrow microenvironment, and hematopoietic progenitors. In particular, hematopoiesis involves a complex interplay of polypeptide growth factors acting via membrane-bound receptors on their target cells. Signaling by growth factors results in cellular proliferation and differentiation, with a response to a particular growth factor often being lineage-specific and/or stage-specific. Development of a single cell type, such as a red blood cell, from a stem cell may require the coordinated action of a plurality of growth factors acting in the proper sequence.

Impaired blood cell production occurs when the proliferation and differentiation of the stem cells or committed cells is disturbed. Impaired blood cell production is the root of hematological disorders. Some of the more common diseases caused by impaired blood cell production, i.e., hematological disorders, include aplastic anemia, hypoplastic anemia, pure red cell aplasia and anemia associated with renal failure or endocrine disorders. Disturbances in the proliferation and differentiation of erythroblasts include defects in DNA synthesis such as impaired utilization of vitamin B12 or folic acid and the megaloblastic anemias, defects in heme or globin synthesis, and anemias of unknown origins such as sideroblastic anemia, anemia associated with chronic infections such as malaria, trypanosomiasis, HIV, hepatitis virus or other viruses, and myelophthisic anemias caused by marrow deficiencies. Impaired blood cell production also affects cancer patients and other autoimmune disease patients who receive bone marrow irradiation or chemotherapy treatment.

Hematological disorders are, thus, a diverse family of disorders embracing clinical and laboratory aspects of a large number of diseases, both malignant and non-malignant. Although some progress has been made in diagnostic and therapeutic strategies to combat hematological disorders, molecular advances are continuing at a rate exceeding the rate of progress in therapeutics. Thus, novel methods for diagnosis and treatment of hematological disorders based on known molecular advances are urgently needed in the field.

SUMMARY OF THE INVENTION

The present invention provides methods and compositions for the diagnosis and treatment of hematological disorders. The present invention is based, at least in part, on the discovery that the 2777 gene is expressed at high levels in hematopoietic cells. Specifically, 2777 is significantly expressed in erythroid cells both in vitro and in vivo. 2777 is also expressed in erythroid progenitor (BFU-E) cells and Glycophorin A positive-lo (GPA-lo) cells in vivo but not in Glycophorin A positive-hi (GPA-hi) cells in vivo (see FIG. 1). Since peptidases belonging to the family of which 2777 is a member are known to degrade peptide hormones, the expression of 2777 in the hematopoietic cells indicates that 2777 is involved in degrading peptide hormones which modulate, e.g., stimulate erythropoiesis. Thus, the 2777 molecules function as modulators of hematopoietic cell activity and are useful as targets and therapeutic agents for the modulation of hematopoietic cell activity, e.g., hematopoietic cell proliferation, and the treatment of hematological disorders.

Accordingly, the present invention provides methods for the diagnosis and treatment of hematological diseases including but not limited to apalstic anemia, hemophilia, sickle cell anemia, thalassemia, blood loss and other blood disorders, e.g., increased blood pressure or blood disorders related to bone marrow irradiation treatments, chemotherapy treatments or compromised kidney function.

In one aspect, the invention provides methods for identifying a compound capable of treating a hematological disorder, e.g., anemia or thalassemia. The method includes assaying the ability of the compound to modulate 2777 nucleic acid expression or 2777 polypeptide activity. In one embodiment, the ability of the compound to modulate nucleic acid expression or 2777 polypeptide activity is determined by detecting modulation of proliferation of a hematopoietic cell. In another embodiment, the ability of the compound to modulate nucleic acid expression or 2777 polypeptide activity is determined by detecting modulation of apoptosis of a hematopoietic cell.

In another aspect, the invention provides methods for identifying a compound capable of modulating a hematological activity, e.g., hematopoietic cell proliferation, differentiation, or cell death. The method includes contacting a cell expressing a 2777 nucleic acid or polypeptide (e.g., a hematopoietic cell) with a test compound and assaying the ability of the test compound to modulate the expression of a 2777 nucleic acid or the activity of a 2777 polypeptide.

Another aspect of the invention provides a method for modulating a hematological activity, e.g., hematopoietic cell proliferation, cell differentiation, or cell death. The method includes contacting a hematopoietic cell with an effective amount of a 2777 modulator, for example, an anti-2777 antibody, a 2777 polypeptide comprising the amino acid sequence of SEQ ID NO:2 or a fragment thereof, a 2777 polypeptide comprising an amino acid sequence which is at least 90 percent identical to the amino acid sequence of SEQ ID NO:2, an isolated naturally occurring allelic variant of a polypeptide consisting of the amino acid sequence of SEQ ID NO:2, a small molecule, an antisense 2777 nucleic acid molecule, a nucleic acid molecule of SEQ ID NO:1 or a fragment thereof, or a ribozyme.

In yet another aspect, the invention features a method for treating a subject having a hematological disorder, e.g., a hematological disorder characterized by aberrant 2777 polypeptide activity or aberrant 2777 nucleic acid expression, e.g., anemia or thalessemia. The method includes administering to the subject a therapeutically effective amount of a 2777 modulator, e.g., in a pharmaceutically acceptable formulation or by using a gene therapy vector. Embodiments of this aspect of the invention include the 2777 modulator being a small molecule, an anti-2777 antibody, a 2777 polypeptide comprising the amino acid sequence of SEQ ID NO:2 or a fragment thereof, a 2777 polypeptide comprising an amino acid sequence which is at least 90 percent identical to the amino acid sequence of SEQ ID NO:2, an isolated naturally occurring allelic variant of a polypeptide consisting of the amino acid sequence of SEQ ID NO:2, an antisense 2777 nucleic acid molecule, a nucleic acid molecule of SEQ ID NO:1 or a fragment thereof, or a ribozyme.

In another aspect, the invention provides a method for modulating, e.g., increasing or decreasing, hematopoietic cell proliferation in a subject by administering to the subject a 2777 modulator in an amount effective for modulating hematopoietic cell proliferation.

Other features and advantages of the invention will be apparent from the following detailed description and claims.

BRIEF DESCRIPTION OF THE DRAWINGS

FIG. 3A-3B depicts the cDNA sequence (SEQ ID NO:1) and amino acid sequence (SEQ ID NO:2) of 2777.

DETAILED DESCRIPTION OF THE DRAWINGS

In eukaryotic cells, most of the cytosolic peptides generated by the proteosome undergo complete degradation by different classes of peptidases. This process of protein degradation is part of the homeostatic mechanism which is essential for the structure and function of the cells (Partaro, F. C. V., et al. (2001) *Eur. J. Biochem.* 268:887–894). Thimet oligopeptidase ("2777") is a known zinc-dependent peptidase member of the metallopeptidase M3 family (Oliveira, V., et al. (2001) *Anal. Biochem.* 292:257–265). This enzyme is a true peptidase and only cleaves short (less than 20 residues) substrates (Smith, A. I., et al. (2000) *Biochem. Soc. Transac.* 28(4):430–434).

2777 is known to be widely distributed in cells and tissues throughout the body. In particular, high levels of 2777 have been localized to the brain, pituitary and testis, with lower levels in other tissues such as the liver, kidney, spleen and lung (Smith, A. I., et al. (2000) *Biochem. Soc. Transac.* 28(4):430–434). The distribution of 2777 in areas rich in neuropeptide content is consistent with a role for this enzyme in the processing/metabolism of bioactive peptides. In fact, studies have shown that 2777 hydrolyzes the biologically active neuropeptide, neurotensin ("NT"), in vitro and in vivo experiments have shown that NT degradation can be blocked by 2777 inhibitors (Oliveira, V., et al. (2001) *Anal. Biochem.* 292:257–265).

However, the ubiquitous distribution of 2777 supports a general function of this enzyme in oligopeptidase metabolism, i.e., a role in both the central and peripheral modulation of a number of biologically important peptides. Studies have shown that 2777 is capable of in vitro degradation or generation of a number of biologically active peptides (other than NT), including dynorphins, gonadotropin-releasing hormone (GnRH) and Substance P. (McCool, S. Pierotti, A. (2000) *DNA Cell Biol.* 19(12): 729–738). 2777 has also been implicated in several physiologically important processes. For example, a number of opioid peptides are substrates for this enzyme, including the novel opioid receptor ligand nociceptin (McCool, S. Pierotti, A. (2000) *DNA Cell Biol.* 19(12):729–738).

Figure 1A:
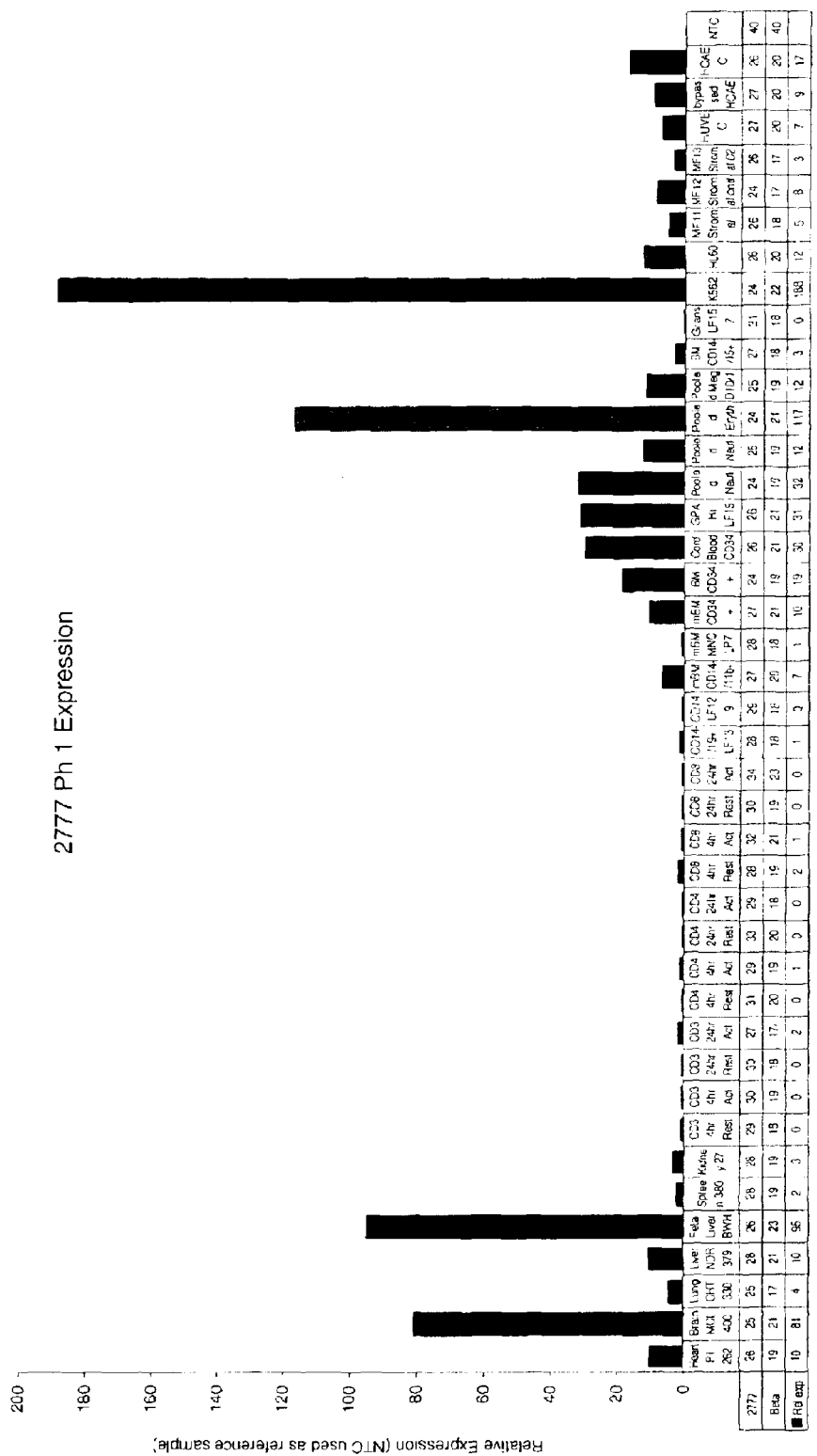
FIGS. 1A–1D are graphs depicting the results of a Taq-Man™ analysis of 2777 cDNA expression in various tissues, cell cultures and cell lines to determine the tissue distribution of the 2777 molecules of the present invention.
Figure 1B:
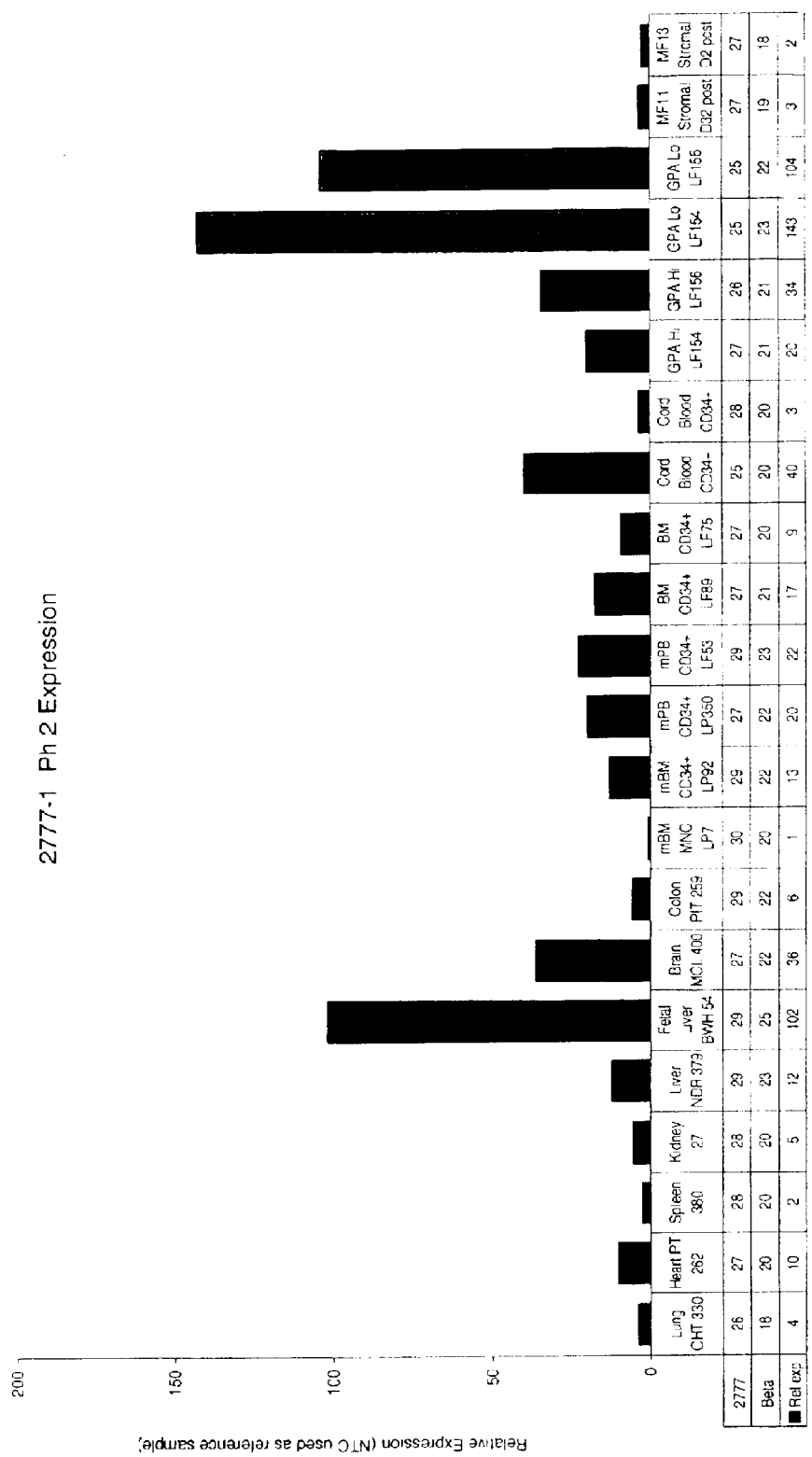
Figure 1C:
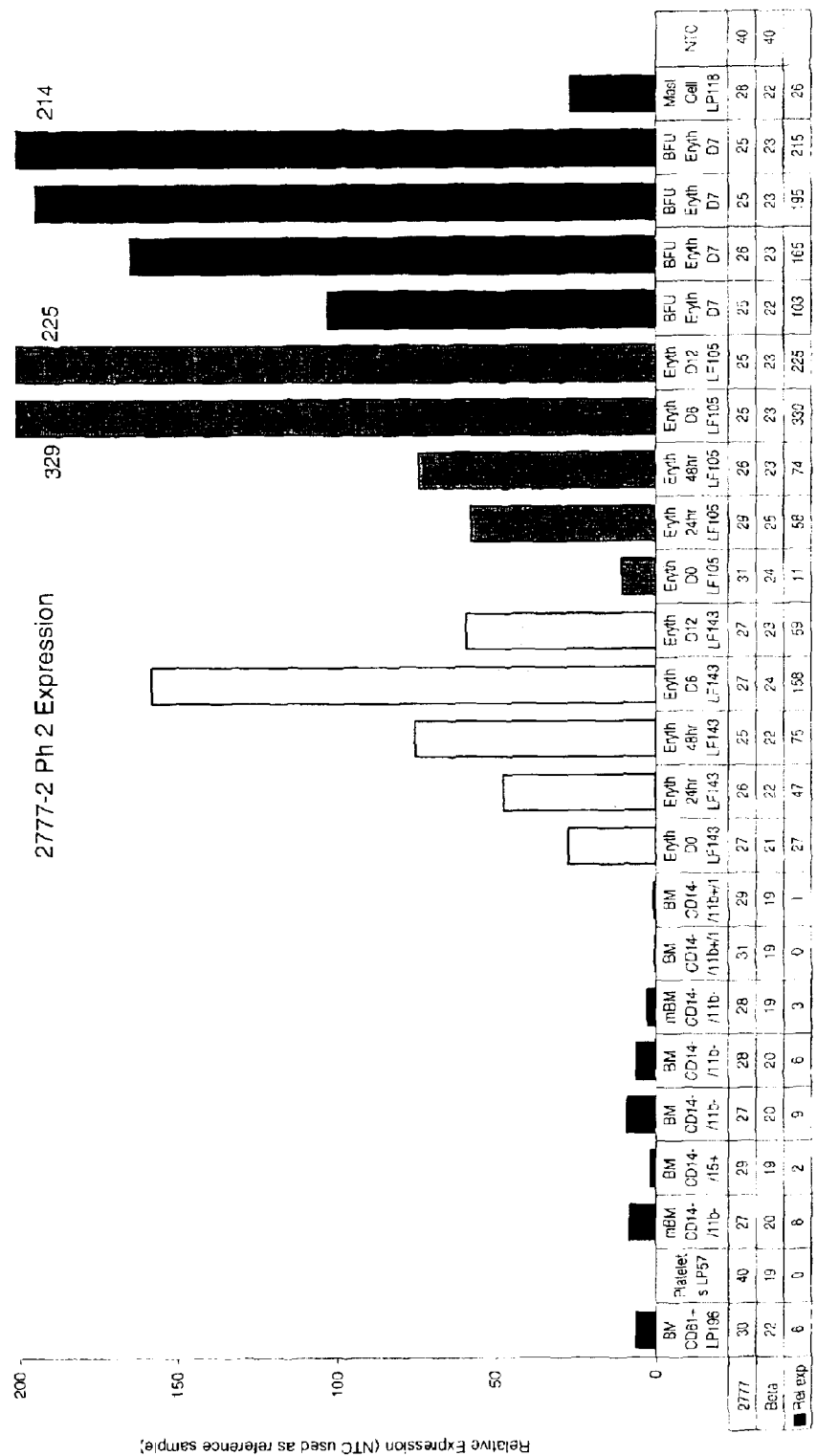
Figure 1D:
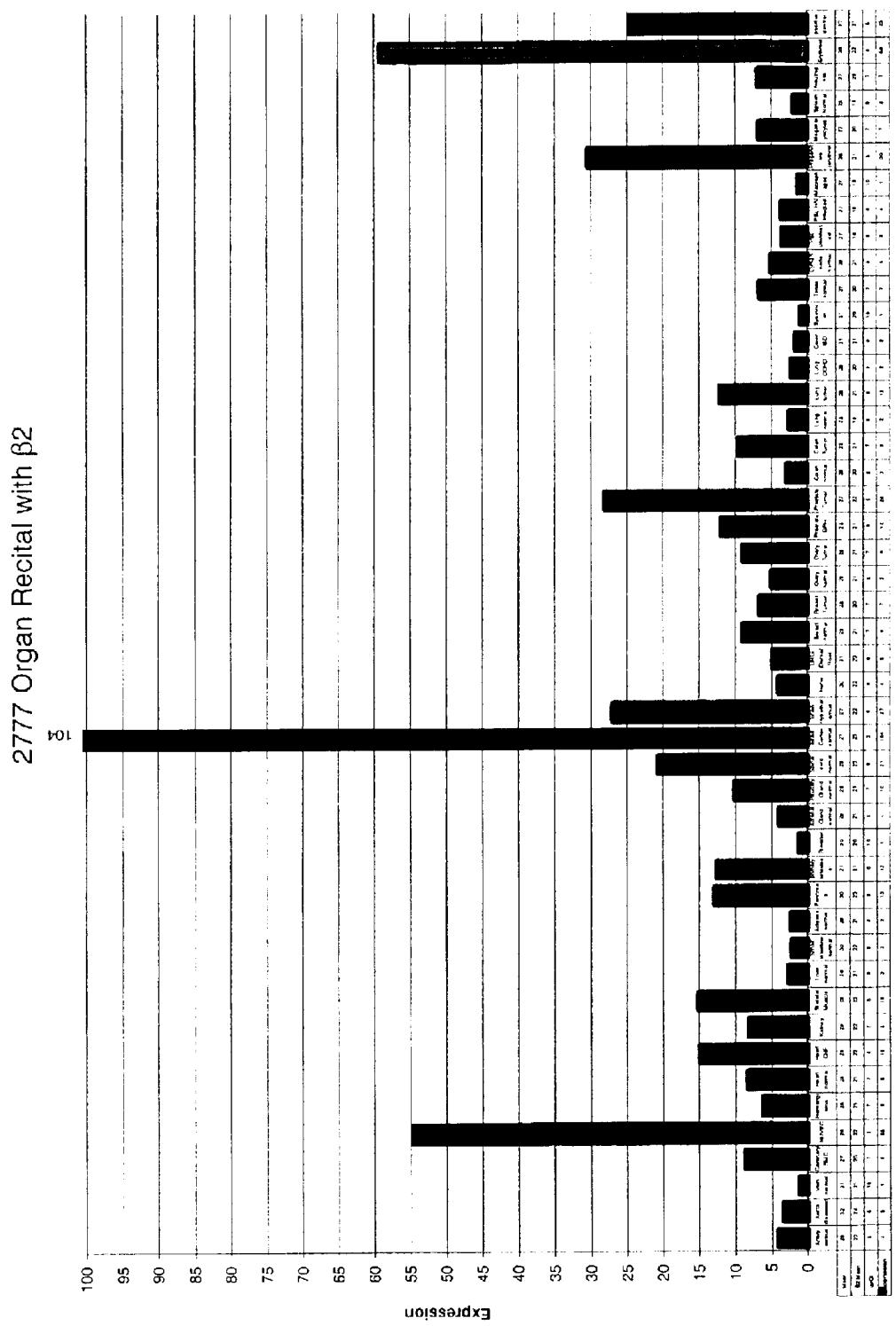
Figure 2:
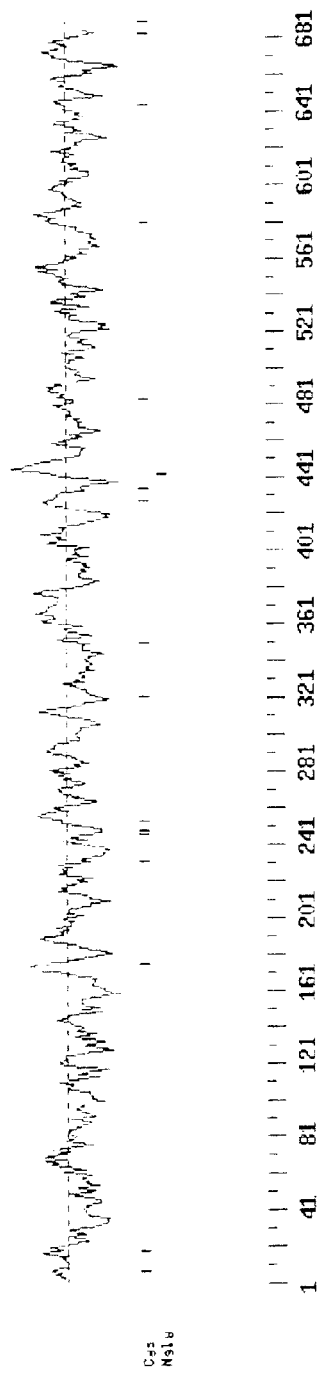
FIG. 2 depicts a structural, hydrophobicity, and antigenicity analysis of the human 2777 protein.

The present invention is based, at least in part, on the heretofore unknown expression of 2777 in hematopoietic cells. Specifically, the present invention demonstrates that 2777 is expressed at high levels in cells of erythroid lineage both in vitro and in vivo. Erythroid cell cultures show increasing levels of 2777 expression up to Day 6 of development (see FIG. 1). 2777 is also expressed at high levels in erythroid progenitor ("BFU-E") cells and Glycophorin A positive-lo ("GPA-lo") in vivo cell populations, but at low levels GPA-hi in vivo cell populations. In organ recital experiments, 2777 was expressed at high levels in the brain, C cells and erythroid cells (see FIG. 1). Glycophorin A protein is known as a late erythroid lineage specific protein. The marked expression of 2777 in GPA-lo cell populations, and the relative non-expression of 2777 in GPA-hi cell populations, indicates that 2777 degrades peptide hormones that stimulate erythropoiesis. Since modulation of erythropoiesis is an important aspect of hematological disorders, modulation of 2777 is an important therapeutic avenue in the treatment of these disorders. Accordingly, the present invention provides methods and compositions for the diagnosis and treatment of hematological disorders.

As used herein, a "hematological disorder" includes a disease, disorder, or condition which affects a hematopoietic cell or tissue. Hematological disorders include diseases, disorders, or conditions associated with aberrant hematological content or function. Hematological disorders can be characterized by a misregulation (e.g., downregulation or upregulation) of 2777 activity. Examples of hematological disorders include disorders resulting from bone marrow irradiation or chemotherapy treatments for cancer, disorders such as Pernicious Anemia, Hemorrhagic Anemia, Hemolytic Anemia, Aplastic Anemia, Sickle Cell Anemia, Sideroblastic Anemia, Anemia associated with chronic infections such as Malaria, Trypanosomiasis, HIV, Hepatitis virus or other viruses, Myelophthisic Anemias caused by marrow deficiencies, renal failure resulting from Anemia, Anemia, Polycethemia, Infectious Mononucleosis (IM), Acute Non-Lymphocytic Leukemia (ANLL), Acute Myeloid Leukemia (AML), Acute Promyelocytic Leukemia (APL), Acute Myelomonocytic Leukemia (AMMoL), Polycethemia Vera, Lymphoma, Acute Lymphocytic Leukemia (ALL), Chronic Lymphocytic Leukemia, Wilm's Tumor, Ewing's Sarcoma, Retinoblastoma, Hemophilia, disorders associated with an increased risk of Thrombosis, Herpes, Thalessemia, antibody-mediated disorders such as transfusion reactions and Erythroblastosis, mechanical trauma to red blood cells such as micro-angiopathic hemolytic anemias, Thrombotic Thrombocytopenic Purpura and disseminated intravascular coagulation, infections by parasites such as Plasmodium, chemical injuries from, e.g., lead poisoning, and Hypersplenism.

As used herein, "2777" encompasses proteins characterized by their ability to modulate signal transduction to thereby modulate hematopoietic cell proliferation or apoptosis in vitro or in vivo. A representative human 2777 cDNA sequence is shown herein in SEQ ID NO:1, and the corresponding amino acid sequence is shown in SEQ ID NO:2. The coding sequence is shown in SEQ ID NO:3. Those skilled in the art will recognize that the illustrated sequences correspond to a single allele of the human 2777 gene, and that allelic variation is expected to exist. Allelic variants include those containing silent mutations and those in which mutations result in amino acid sequence changes. It will also be evident that one skilled in the art could create additional variants, such as by engineering sites that would facilitate manipulation of the nucleotide sequence using alternative codons, by substitution of codons to produce conservative changes in amino acid sequence, etc. The use of allelic and engineered variant 2777s is contemplated by the present invention. The use of 2777 molecules from non-human species are also contemplated by the present invention.

The present invention provides methods and compositions for the diagnosis and treatment of hematological disorders. The 2777 modulators identified according to the methods of the invention can be used to modulate hematopoietic cell proliferation and are, therefore, useful in treating or diagnosing hematological disorders. For example, inhibition of the activity of a 2777 molecule (e.g., using a 2777 modulator identified using the screening assays described herein) can cause increased hematopoietic cell proliferation and, therefore, increased blood cell production in a subject, thereby preventing hematological disorders such as aplastic anemia or sickle cell anemia in a subject.

Alternatively, stimulation of the activity of a 2777 molecule (e.g., using a 2777 modulator identified using the screening assays described herein) can cause decreased hematopoietic cell proliferation and, therefore, decreased blood cell production in a subject, thereby preventing hematological disorders such as hemorrhagic anemia, polycethemia, infectious mononucleosis or leukemia in a subject.

As used interchangeably herein, "2777 activity," "biological activity of 2777" or "functional activity of 2777," includes an activity exerted by a 2777 protein, polypeptide or nucleic acid molecule on a 2777 responsive cell or tissue, e.g., a hematopoietic cell, or on a 2777 protein substrate, as determined in vivo, or in vitro, according to standard techniques. 2777 activity can be a direct activity, such as an association with a 2777-target molecule. As used herein, a "substrate" or "target molecule" or "binding partner" is a molecule with which a 2777 protein binds or interacts in nature, such that 2777-mediated function, e.g., modulation of apoptosis or modulation of cell proliferation, is achieved. A 2777 target molecule can be a non-2777 molecule or a 2777 protein or polypeptide. Examples of such target molecules include proteins in the same signaling path as the 2777 protein, e.g., proteins which may function upstream (including both stimulators and inhibitors of activity) or downstream of the 2777 protein in a pathway involving regulation of hematopoietic cell proliferation or apoptosis. Alternatively, a 2777 activity is an indirect activity, such as a cellular signaling activity mediated by interaction of the 2777 protein with a 2777 target molecule. The biological activities of 2777 are described herein. For example, the 2777 proteins can have one or more of the following activities: (1) they modulate hematopoietic cell proliferation; (2) they modulate apoptosis of hematopoietic cells; and (3) they modulate degradation of peptide hormones involved in erythropoiesis.

As used herein, the term "hematopoietic cell" includes yolk sac stem cells, primitive erythroid cells, fetal liver cells, fetal spleen cells, fetal bone marrow cells, non-fetal bone marrow cells, megakaryocytes, stem cells, lymphoid stem cells, myeloid stem cells, progenitor cells, progenitor lymphocytes, progenitor T lymphocytes, progenitor B lymphocytes, progenitor erythrocytes, progenitor neutrophils, progenitor eosinophils, progenitor basophils, progenitor monocytes, progenitor mast cells, progenitor platelets, committed lymphocytes, committed T lymphocytes, committed B lymphocytes, committed erythrocytes, committed neutrophils, committed eosinophils, committed basophils, committed monocytes, committed mast cells, committed platelets, differentiated lymphocytes, differentiated T lymphocytes, differentiated B lymphocytes, differentiated erythrocytes, differentiated neutrophils, differentiated eosinophils, differentiated basophils, differentiated monocytes, differentiated mast cells, differentiated platelets, mature lymphocytes, mature T lymphocytes, mature B lymphocytes, mature erythrocytes, mature neutrophils, mature eosinophils, mature basophils, mature monocytes, mature mast cells, and mature platelets.

As used herein, the term "progenitor cell" includes any somatic cell which has the capacity to generate fully differentiated, functional progeny by differentiation and proliferation. Progenitor cells include progenitors from any tissue or organ system, including, but not limited to, blood, nerve, muscle, skin, gut, bone, kidney, liver, pancreas, thymus, and the like. Progenitor cells are distinguished from "committed cells" and "differentiated cells," which are defined as those cells which may or may not have the capacity to proliferate, i.e., self-replicate, but which are unable to undergo further differentiation to a different cell type under normal physiological conditions. Moreover, progenitor cells are further distinguished from abnormal cells such as cancer cells, especially leukemia cells, which proliferate (self-replicate) but which generally do not further differentiate, despite appearing to be immature or undifferentiated.

Progenitor cells include all the cells in a lineage of differentiation and proliferation prior to the most differentiated or the fully mature cell. Thus, for example, progenitors include the skin progenitor in the mature individual, which is capable of differentiation to only one type of cell, but which is itself not fully mature or fully differentiated. Production of mature, functional blood cells results from proliferation and differentiation of "unipotential progenitors," i.e., those progenitors which have the capacity to make only one type of one type of blood cell. For red blood cell production, a progenitor called a "CFU-E" (colony forming unit-erythroid) has the capacity to generate two to 32 progeny cells.

Various other hematopoietic progenitors have been characterized. For example, hematopoietic progenitor cells include those cells which are capable of successive cycles of differentiating and proliferating to yield up to eight different mature hematopoietic cell lineages. At the most primitive or undifferentiated end of the hematopoietic spectrum, hematopoietic progenitor cells include the hematopoietic "stem cells." These rare cells, which represent 1 in 10,000 to 1 in 100,000 of cells in the bone marrow, each have the capacity to generate a billion mature blood cells of all lineages and are responsible for sustaining blood cell production over the life of an animal. They reside in the marrow primarily in a quiescent state and may form identical daughter cells through a process called self-renewal. Accordingly, such an uncommitted progenitor can be described as being "totipotent," i.e., both necessary and sufficient for generating all types of mature blood cells. Progenitor cells which retain a capacity to generate all blood cell lineages but which can not self-renew are termed "pluripotent." Cells which can produce some but not all blood lineages and can not self-renew are termed "multipotent."

As used herein, "hematopoietic cell activity" includes an activity exerted by a hematopoietic cell, or an activity that takes place in a hematopoietic cell. For example, such activities include cellular processes that contribute to the physiological role of hematopoietic cells, such as hematopoiesis, but are not limited to, cell proliferation, differentiation, growth, migration and programmed cell death.

As used herein, the term "modulate" includes alteration of, e.g., by increasing or decreasing the particular parameter being described, e.g., 2777 activity.

As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage.

I. Screening Assays:

The invention provides methods (also referred to herein as "screening assays") for identifying modulators, i.e., candidate or test compounds or agents (e.g., peptides, peptidomimetics, small molecules, ribozymes, or 2777 antisense molecules) which bind to 2777 proteins, have a stimulatory or inhibitory effect on 2777 expression or 2777 activity, or have a stimulatory or inhibitory effect on the expression or activity of a 2777 target molecule. Compounds identified using the assays described herein may be useful for treating hematological disorders.

Candidate/test compounds include, for example, 1) peptides such as soluble peptides, including Ig-tailed fusion peptides and members of random peptide libraries (see, e.g., Lam, K. S. et al. (1991) *Nature* 354:82–84; Houghten, R. et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

Assays that may be used to identify compounds that modulate 2777 activity include assays for cytochrome C release from mitochondria during cell apoptosis, e.g., hematopoietic cell apoptosis (as described in, for example, Bossy-Wetzel E. et al. (2000) *Methods in Enzymol.* 322:235–42); cytofluorometric quantitation of nuclear apoptosis induced in a cell-free system (as described in, for example, Lorenzo H. K. et al. (2000) *Methods in Enzymol.* 322:198–201); apoptotic nuclease assays (as described in, for example, Hughes F. M. (2000) *Methods in Enzymol.* 322:47–62); analysis of apoptotic cells, e.g., apoptotic hematopoietic cells, by flow and laser scanning cytometry (as described in, for example, Darzynkiewicz Z. et al. (2000) *Methods in Enzymol.* 322:18–39); detection of apoptosis by annexin V labeling (as described in, for example, Bossy-Wetzel E. et al. (2000) *Methods in Enzymol.* 322:15–18); transient transfection assays for cell death genes (as described in, for example, Miura M. et al. (2000) *Methods in Enzymol.* 322:480–92); and assays that detect DNA cleavage in apoptotic cells, e.g., apoptotic hematopoietic cells (as described in, for example, Kauffman S. H. et al. (2000) *Methods in Enzymol.* 322:3–15).

Assays that may be used to identify the peptidase activity of 2777, e.g., hydrolysis of biologically active peptides by 2777, include Fluorimetric enzyme assays as described in Molina et al. (2000) *Life Sciences* 67:509–520; HPLC analysis of hydrolyzed peptides as described in Molina et al. (2000) *Life Sciences* 67:509–520; peptidase assays as described in Saric, T., et al. (2001) *J. Biol. Chem.* 276(39): 36474–36481 (2777 activity was analyzed using the quenched fluorogenic substrate); kinetic assays as described in Oliveira, V. (2001) *Biochemistry* 40:4417–4425; measurement of peptidase activity, e.g., 2777 activity, and statistical analysis as described in Smith, A. I., et al. (2000) *Biochemical Society* 28(4):430–434; and kinetic assays, determination of bonds cleaved by 2777 and the amino acid analysis (to determine the amino acid compositions and the concentration of 2777) as described in Oliveira, V., (2001) *Anal. Biochem* 292:257–265.

Proliferation assays that may be used to identify compounds that modulate 2777 activity include assays using 32D cells (a multi-lineage murine hematopoietic cell line) as described in U.S. Pat. No. 6,231,880, the contents of which are incorporated herein by reference. Cell proliferation assays which measure the growth phenotype of cells with an ablated growth regulatory gene of interest, e.g., 2777 are described in Sudershan, C., et al. (1998) *J. Cell. Physiol.* 176:67–75. The ability of a test compound to modulate 2777 activity may also be determined by monitoring cellular processes such as cell division, protein synthesis, nucleic acid (DNA or RNA) synthesis, nucleic acid (principally DNA) fragmentation and apoptosis.

In one aspect, an assay is a cell-based assay in which a cell which expresses a 2777 protein, or biologically active portion thereof, that is believed to be involved in the modulation of hematopoietic cell proliferation of hematopoietic cells is contacted with a test compound and the ability of the test compound to modulate 2777 activity is determined. In a preferred embodiment, the biologically active portion of the 2777 protein includes a domain or motif that can modulate apoptosis of hematopoietic cells and/or which can modulate hematopoietic cell proliferation. Determining the ability of the test compound to modulate 2777 activity can be accomplished by monitoring, for example, the production of one or more specific metabolites in a cell which expresses 2777 (see, e.g., Saada et al. (2000) *Biochem Biophys. Res. Commun.* 269: 382–386) or by monitoring cell death, cell proliferation, or cell differentiation in the cell. The cell, for example, can be of mammalian origin, e.g., a hematopoietic cell such as a committed erythrocyte or a progenitor cell.

The ability of the test compound to modulate 2777 binding to a substrate or to bind to 2777 can also be determined. Determining the ability of the test compound to modulate 2777 binding to a substrate can be accomplished, for example, by coupling the 2777 substrate with a radioisotope or enzymatic label such that binding of the 2777 substrate to 2777 can be determined by detecting the labeled 2777 substrate in a complex. Alternatively, 2777 could be coupled with a radioisotope or enzymatic label to monitor the ability of a test compound to modulate 2777 binding to a 2777 substrate in a complex. Determining the ability of the test compound to bind 2777 can be accomplished, for example, by coupling the compound with a radioisotope or enzymatic label such that binding of the compound to 2777 can be determined by detecting the labeled 2777 compound in a complex. For example, 2777 substrates can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to interact with 2777 without the labeling of any of the interactants. For example, a microphysiometer can be used to detect the interaction of a compound with 2777 without the labeling of either the compound or the 2777 (McConnell, H. M. et al. (1992) *Science* 257:1906–1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 2777.

The ability of a 2777 modulator to modulate, e.g., inhibit or increase, 2777 activity can also be determined through screening assays which identify modulators which either increase or decrease apoptosis and cell proliferation. In one embodiment, the invention provides for a screening assay involving contacting cells which express a 2777 protein or polypeptide with a test compound, and examining the cells for the morphological features of apoptosis. For example, cells expressing a 2777 protein or polypeptide can be contacted with a test compound and nuclearly stained with acridine orange. Subsequently, nuclear DNA can be extracted and analyzed for DNA fragmentation as described in Inohora et al., (1997) *EMBO J.* 16:1686–1694.

To determine whether a test compound modulates 2777 expression, in vitro transcriptional assays can be performed. To perform such an assay, the full length promoter and enhancer of 2777 can be linked to a reporter gene such as chloramphenicol acetyltransferase (CAT) and introduced into host cells. The same host cells can then be transfected with the test compound. The effect of the test compound can be measured by testing CAT activity and comparing it to CAT activity in cells which do not contain the test compound. An increase or decrease in CAT activity indicates a modulation of 2777 expression and is, therefore, an indicator of the ability of the test compound to modulate hematopoietic cell proliferation.

In yet another embodiment, an assay of the present invention is a cell-free assay in which a 2777 protein or biologically active portion thereof (e.g., (e.g., the 2777 gene without the twenty-two amino terminus amino acids) is contacted with a test compound and the ability of the test compound to bind to or to modulate (e.g., stimulate or inhibit) the activity of the 2777 protein or biologically active portion thereof is determined. Preferred biologically active portions of the 2777 proteins to be used in assays of the present invention include fragments which participate in interactions with non-2777 molecules, e.g., fragments with high surface probability scores. Binding of the test compound to the 2777 protein can be determined either directly or indirectly as described above. Determining the ability of the 2777 protein to bind to a test compound can also be accomplished using a technology such as real-time Biomolecular Interaction Analysis (BIA) (Sjolander, S. and Urbaniczky, C. (1991) *Anal. Chem.* 63:2338–2345; Szabo et al. (1995) *Curr. Opin. Struct. Biol.* 5:699–705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In more than one embodiment of the above assay methods of the present invention, it may be desirable to immobilize either 2777 or a 2777 target molecule to facilitate separation of complexed from uncomplexed forms of one or both of the proteins, as well as to accommodate automation of the assay. Binding of a test compound to a 2777 protein, or interaction of a 2777 protein with a 2777 target molecule in the presence and absence of a test compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/2777 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or 2777 protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of 2777 binding or activity determined using standard techniques.

Other techniques for immobilizing proteins on matrices can also be used in the screening assays of the invention. For example, either a 2777 protein or a 2777 target molecule can be immobilized utilizing conjugation of biotin and streptavidin. Biotinylated 2777 protein or target molecules can be prepared from biotin-NHS (N-hydroxysuccinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with 2777 protein or target molecules but which do not interfere with binding of the 2777 protein to its target molecule can be derivatized to the wells of the plate, and unbound target or 2777 protein is trapped in the wells by antibody conjugation. Methods for detecting such complexes, in addition to those described above for the GST-immobilized complexes, include immunodetection of complexes using antibodies reactive with the 2777 protein or target molecule, as well as enzyme-linked assays which rely on detecting an enzymatic activity associated with the 2777 protein or target molecule.

In yet another aspect of the invention, the 2777 protein or fragments thereof (e.g., the N-terminal region of the 2777 protein that is believed to be involved in the regulation of apoptotic activity) can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 2777 ("2777-binding proteins" or "2777-bp) and are involved in 2777 activity. Such 2777-binding proteins are also likely to be involved in the propagation of signals by the 2777 proteins or 2777 targets as, for example, downstream elements of a 2777-mediated signaling pathway. Alternatively, such 2777-binding proteins are likely to be 2777 inhibitors.

The two-hybrid system is based on the modular nature of most transcription factors, which consist of separable DNA-binding and activation domains. Briefly, the assay utilizes two different DNA constructs. In one construct, the gene that codes for a 2777 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a 2777-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 2777 protein.

In another aspect, the invention pertains to a combination of two or more of the assays described herein. For example, a modulating agent can be identified using a cell-based or a cell-free assay, and the ability of the agent to modulate the activity of a 2777 protein can be confirmed in vivo, e.g., in an animal such as an animal model for aplastic anemia, sickle cell anemia, thalessemia or sideroblastic anemia. Examples of animals that can be used include, for example, the C57 mouse model for testing whether a compound has in vivo activity in stimulating erythropoiesis as described in U.S. Pat. No. 6,231,880 (also describes cell proliferation stimulation induced by hematopoietic growth factors in baboons); the transgenic mouse model for bone marrow transplantation for sickle cell anemia as described in Iannone, R. et al., (2001) *Blood* 97(12):3960–3965; the rat model for Aplastic Anemia as described in Santiago, S. et al. (2001) *Transplant Proc.* 33(4):2600–2602; transgenic animal models to screen for fetal hemoglobin-stimulating compounds as described in Fibach, E. (2001) *Semin Hematol* 38(4):374–381; mouse models for the treatment of autoimmune diseases by hematopoietic stem cell transplantation as described in Ikehara, S. (2001) *Experimental Hematology* 29:661–669 (specifically, mice with thrombocytic purpura, thrombocytopenia, renal failure, hemolytic anemia, systemic lupus erythematosus, hemolytic anemia, sjogren syndrome, rheumatoid arthritis, pancreatitis, sialoadentis, autoimmune hepatitis, myocardial infarcton, insulin-dependent diabetes mellitus, non-insulin-dependent diabetes mellitus and fogal segmental glomerular sclerosis are described); the three mouse models with globin gene mutations resulting in human thalessemia as described in Martinell, J., et al. (1981) *Proc. Natl. Acad. Sci.* 78(8): 5056–5060; animal models for X-linked Sideroblastic Anemia as described in Yamamoto, M. et al., (2000) *Intl. J. Hematology Review* 72:157–164; the mouse model for anemic yolk sacs as described in Martin, J. S., et al. (1995) *Ann. N. Y. Acad. Sci.* 752:300–8; various animal models for sickle cell anemia as described in Nagel. R. L. (2001) *Brit J. Hematol.* 112:19–25 (specifically, models with a combination of murine globins and human globin chains, the NYC1 model, the S+S Antilles model, and transgenic models with exclusively human globin chains are described); and animal models of cyclic hematopoiesis as described in Jones, J. B. & Lange, R. D. (1983) *Exp. Hematol.* 11(7):571–580. Additionally, transgenic animals for the Human Beta Globin Gene Locus as described in U.S. Pat. No. 6,231,880 may be used.

Moreover, a 2777 modulator identified as described herein (e.g., an antisense 2777 nucleic acid molecule, a 2777-specific antibody, or a small molecule) can be used in an animal model to determine the efficacy, toxicity, or side effects of treatment with such a modulator. Alternatively, a 2777 modulator identified as described herein can be used in an animal model to determine the mechanism of action of such a modulator.

II. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining 2777 protein and/or nucleic acid expression as well as 2777 activity, in the context of a biological sample (e.g., blood) to thereby determine whether an individual is afflicted with a hematological disorder. The invention also provides for prognostic (or predictive) assays for determining whether an individual is at risk of developing a hematological disorder. For example, mutations in a 2777 gene can be assayed for in a biological sample. Such assays can be used for prognostic or predictive purpose to thereby phophylactically treat an individual prior to the onset of a hematological disorder.

Another aspect of the invention pertains to monitoring the influence of 2777 modulators (e.g., anti-2777 antibodies or 2777 ribozymes) on the expression or activity of 2777 in clinical trials.

These and other agents are described in further detail in the following sections.

A. Diagnostic Assays for Hematological Disorders

To determine whether a subject is afflicted with a hematological disorder, a biological sample may be obtained from a subject and the biological sample may be contacted with a compound or an agent capable of detecting a 2777 protein or nucleic acid (e.g., mRNA or genomic DNA) that encodes a 2777 protein, in the biological sample. A preferred agent for detecting 2777 mRNA or genomic DNA is a labeled nucleic acid probe capable of hybridizing to 2777 mRNA or genomic DNA. The nucleic acid probe can be, for example, the 2777 nucleic acid set forth in SEQ ID NO:1, or a portion thereof, such as an oligonucleotide of at least 15, 20, 25, 30, 25, 40, 45, 50, 100, 250 or 500 nucleotides in length and sufficient to specifically hybridize under stringent conditions to 2777 mRNA or genomic DNA. Other suitable probes for use in the diagnostic assays of the invention are described herein.

A preferred agent for detecting 2777 protein in a sample is an antibody capable of binding to 2777 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect 2777 mRNA, protein, or genomic DNA in a biological sample in vitro as well as in vivo. For example, in vitro techniques for detection of 2777 mRNA include Northern hybridizations and in situ hybridizations. In vitro techniques for detection of 2777 protein include enzyme linked immunosorbent assays (ELISAs), Western blots, immunoprecipitations and immunofluorescence. In vitro techniques for detection of 2777 genomic DNA include Southern hybridizations. Furthermore, in vivo techniques for detection of 2777 protein include introducing into a subject a labeled anti-2777 antibody. For example, the antibody can be labeled with a radioactive marker whose presence and location in a subject can be detected by standard imaging techniques.

In another embodiment, the methods further involve obtaining a control biological sample from a control subject, contacting the control sample with a compound or agent capable of detecting 2777 protein, mRNA, or genomic DNA, such that the presence of 2777 protein, mRNA or genomic DNA is detected in the biological sample, and comparing the presence of 2777 protein, mRNA or genomic DNA in the control sample with the presence of 2777 protein, mRNA or genomic DNA in the test sample.

B. Prognostic Assays for Hematological Disorders

The present invention further pertains to methods for identifying subjects having or at risk of developing a hematological disorder associated with aberrant 2777 expression or activity.

As used herein, the term "aberrant" includes a 2777 expression or activity which deviates from the wild type 2777 expression or activity. Aberrant expression or activity includes increased or decreased expression or activity, as well as expression or activity which does not follow the wild type developmental pattern of expression or the subcellular pattern of expression. For example, aberrant 2777 expression or activity is intended to include the cases in which a mutation in the 2777 gene causes the 2777 gene to be under-expressed or over-expressed and situations in which such mutations result in a non-functional 2777 protein or a protein which does not function in a wild-type fashion, e.g., a protein which does not interact with a 2777 substrate, or one which interacts with a non-2777 substrate.

The assays described herein, such as the preceding diagnostic assays or the following assays, can be used to identify a subject having or at risk of developing a hematological disorder, e.g., aplastic anemia, Sickle Cell Anemia, polycythemia or leukemia. A biological sample may be obtained from a subject and tested for the presence or absence of a genetic alteration. For example, such genetic alterations can be detected by ascertaining the existence of at least one of 1) a deletion of one or more nucleotides from a 2777 gene, 2) an addition of one or more nucleotides to a 2777 gene, 3) a substitution of one or more nucleotides of a 2777 gene, 4) a chromosomal rearrangement of a 2777 gene, 5) an alteration in the level of a messenger RNA transcript of a 2777 gene, 6) aberrant modification of a 2777 gene, such as of the methylation pattern of the genomic DNA, 7) the presence of a non-wild type splicing pattern of a messenger RNA transcript of a 2777 gene, 8) a non-wild type level of a 2777-protein, 9) allelic loss of a 2777 gene, and 10) inappropriate post-translational modification of a 2777-protein.

As described herein, there are a large number of assays known in the art which can be used for detecting genetic alterations in a 2777 gene. For example, a genetic alteration in a 2777 gene may be detected using a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in a 2777 gene (see Abravaya et al. (1995) *Nucleic Acids Res.* 23:675–682). This method includes collecting a biological sample from a subject, isolating nucleic acid (e.g., genomic DNA, mRNA or both) from the sample, contacting the nucleic acid sample with one or more primers which specifically hybridize to a 2777 gene under conditions such that hybridization and amplification of the 2777 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA* 87:1874–1878), transcriptional amplification system (Kwoh, D. Y. et al. (1989) *Proc. Natl. Acad. Sci. USA* 86:1173–1177), Q-Beta Replicase (Lizardi, P. M. et al.

(1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a 2777 gene from a biological sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 2777 can be identified by hybridizing biological sample derived and control nucleic acids, e.g., DNA or RNA, to high density arrays containing hundreds or thousands of oligonucleotide probes (Cronin, M. T. et al. (1996) *Human Mutation* 7:244–255; Kozal, M. J. et al. (1996) *Nature Medicine* 2:753–759). For example, genetic mutations in 2777 can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential, overlapping probes. This step allows for the identification of point mutations. This step is followed by a second hybridization array that allows for the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 2777 gene in a biological sample and detect mutations by comparing the sequence of the 2777 in the biological sample with the corresponding wild-type (control) sequence. Examples of sequencing reactions include those based on techniques developed by Maxam and Gilbert (1977) *Proc. Natl. Acad. Sci. USA* 74:560) or Sanger (1977) *Proc. Natl. Acad. Sci. USA* 74:5463). It is also contemplated that any of a variety of automated sequencing procedures can be utilized when performing the diagnostic assays (Naeve, C. W. (1995) *Biotechniques* 19:448–53), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the 2777 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type 2777 sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397 and Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in 2777 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a 2777 sequence, e.g., a wild-type 2777 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in 2777 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766; see also Cotton (1993) *Mutat. Res.* 285:125–144 and Hayashi (1992) *Genet. Anal. Tech. Appl.* 9:73–79). Single-stranded DNA fragments of sample and control 2777 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

Furthermore, the prognostic assays described herein can be used to determine whether a subject can be administered a 2777 modulator (e.g., an agonist, antagonist, peptidomimetic, protein, peptide, nucleic acid, or small molecule) to effectively treat a hematological disorder.

C. Monitoring of Effects During Clinical Trials

The present invention further provides methods for determining the effectiveness of a 2777 modulator (e.g., a 2777 modulator identified herein) in treating a hematological disorder in a subject. For example, the effectiveness of a 2777 modulator in increasing 2777 gene expression, protein levels, or in upregulating 2777 activity, can be monitored in clinical trials of subjects exhibiting decreased 2777 gene expression, protein levels, or downregulated 2777 activity. Alternatively, the effectiveness of a 2777 modulator in decreasing 2777 gene expression, protein levels, or in down-regulating 2777 activity, can be monitored in clinical trials of subjects exhibiting increased 2777 gene expression, protein levels, or 2777 activity. In such clinical trials, the expression or activity of a 2777 gene, and preferably, other genes that have been implicated in, for example, a hematological disorder can be used as a "read out" or marker of the phenotype of a particular cell.

For example, and not by way of limitation, genes, including 2777, that are modulated in cells by treatment with an agent which modulates 2777 activity (e.g., identified in a screening assay as described herein) can be identified. Thus, to study the effect of agents which modulate 2777 activity on subjects suffering from a hematological disorder in, for example, a clinical trial, cells can be isolated and RNA prepared and analyzed for the levels of expression of 2777 and other genes implicated in the hematological disorder. The levels of gene expression (e.g., a gene expression pattern) can be quantified by Northern blot analysis or RT-PCR, as described herein, or alternatively by measuring the amount of protein produced, by one of the methods described herein, or by measuring the levels of activity of 2777 or other genes. In this way, the gene expression pattern can serve as a marker, indicative of the physiological response of the cells to the agent which modulates 2777 activity. This response state may be determined before, and at various points during treatment of the individual with the agent which modulates 2777 activity.

In a preferred embodiment, the present invention provides a method for monitoring the effectiveness of treatment of a subject with an agent which modulates 2777 activity (e.g., an agonist, antagonist, peptidomimetic, protein, peptide, nucleic acid, or small molecule identified by the screening assays described herein) including the steps of (i) obtaining a pre-administration sample from a subject prior to administration of the agent; (ii) detecting the level of expression of a 2777 protein, mRNA, or genomic DNA in the pre-administration sample; (iii) obtaining one or more post-administration samples from the subject; (iv) detecting the level of expression or activity of the 2777 protein, mRNA, or genomic DNA in the post-administration samples; (v) comparing the level of expression or activity of the 2777 protein, mRNA, or genomic DNA in the pre-administration sample with the 2777 protein, mRNA, or genomic DNA in the post administration sample or samples; and (vi) altering the administration of the agent to the subject accordingly. For example, increased administration of the agent may be desirable to increase the expression or activity of 2777 to higher levels than detected, i.e., to increase the effectiveness of the agent. Alternatively, decreased administration of the agent may be desirable to decrease expression or activity of 2777 to lower levels than detected, i.e. to decrease the effectiveness of the agent. According to such an embodiment, 2777 expression or activity may be used as an indicator of the effectiveness of an agent, even in the absence of an observable phenotypic response.

III. Methods of Treatment of Subjects Suffering from Hematological Disorders:

The present invention provides for both prophylactic and therapeutic methods of treating a subject, e.g., a human, at risk of (or susceptible to) a hematological disorder such as aplastic anemia, Sickle Cell Anemia, polycythemia or leukemia. With regard to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype").

Thus, another aspect of the invention provides methods for tailoring an subject's prophylactic or therapeutic treatment with either the 2777 molecules of the present invention or 2777 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

A. Prophylactic Methods

In one aspect, the invention provides a method for preventing in a subject, a hematological disorder by administering to the subject an agent which modulates 2777 expression or 2777 activity, e.g., modulation of hematopoietic cell proliferation of hematopoietic cells. Subjects at risk for a hematological disorder can be identified by, for example, any or a combination of the diagnostic or prognostic assays described herein. Administration of a prophylactic agent can occur prior to the manifestation of symptoms characteristic of aberrant 2777 expression or activity, such that a hematological disorder is prevented or, alternatively, delayed in its progression. Depending on the type of 2777 aberrancy, for example, a 2777, 2777 agonist or 2777 antagonist agent can be used for treating the subject. The appropriate agent can be determined based on screening assays described herein.

B. Therapeutic Methods

Another aspect of the invention pertains to methods for treating a subject suffering from a hematological disorder. These methods involve administering to a subject an agent which modulates 2777 expression or activity (e.g., an agent identified by a screening assay described herein), or a combination of such agents. In another embodiment, the method involves administering to a subject a 2777 protein or nucleic acid molecule as therapy to compensate for reduced, aberrant, or unwanted 2777 expression or activity.

Stimulation of 2777 activity is desirable in situations in which 2777 is abnormally downregulated and/or in which increased 2777 activity is likely to have a beneficial effect, e.g., a decrease in the proliferation of hematopoietic cells, thereby ameliorating hematological disorders such as polycytemia or infectious mononucleosis in a subject. Likewise, inhibition of 2777 activity is desirable in situations in which 2777 is abnormally upregulated and/or in which decreased 2777 activity is likely to have a beneficial effect, e.g., an increase in hematopoietic cell proliferation, thereby ameliorating a hematological disorder such as aplastic anemia or hemorrhagic anemia in a subject.

1. Pharmaceutical Compositions

The agents which modulate 2777 activity can be administered to a subject using pharmaceutical compositions suitable for such administration. Such compositions typically comprise the agent (e.g., nucleic acid molecule, protein, or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates 2777 activity (e.g., a fragment of a 2777 protein or an anti-2777 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate 2777 activity can also be prepared in the form of suppositories (e.g., with conventional suppository bases such as cocoa butter and other glycerides) or retention enemas for rectal delivery.

In one embodiment, the agents that modulate 2777 activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates 2777 activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such 2777 modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

2. Transplantation and Transfusions

The present invention provides methods for increasing hematopoietic cells in patients, particularly patients undergoing radiation therapy and/or chemotherapy, e.g., in the treatment of cancer. Such therapies kill dividing progenitor cells in the marrow and peripheral blood, limiting therapy and often requiring transfusions to restore circulating levels of platelets and other blood cells. Of particular interest are those patients receiving bone marrow and/or peripheral blood stem cell transplants following radiation therapy and patients suffering from congenital metabolic defects necessitating bone marrow transplant. Among these indications are bone marrow transplants associated with the treatment of breast cancer, leukemia, lymphoma, multiple myeloma, and congenital defects such as severe combined immune deficiency, thallasemia, and sickle cell anemia. Peripheral blood stem cell transplantation may be preferred in conditions where a risk of tumor cells in the blood is not present.

As used herein, the term "transplantation" includes the process of removing cells from a donor subject and subsequently administering the cells to a recipient subject. The term encompasses both allogeneic transplantation, wherein the donor and recipient are different subjects of the same species; and autologous transplantation, wherein the donor and recipient are the same subject.

Methods for carrying out bone marrow and peripheral blood stem cell transplants are known in the art. (Snyder et al., "Transfusion Medicine" in Benz and McArthur, eds., *Hematology* 1994, American Society of Hematology, 96–106, 1994.) For example, peripheral blood stem cells are collected by leukapheresis according to accepted clinical procedures. Hematopoietic progenitor cells can be selected on the basis of cell surface markers (e.g. CD34), allowing for enrichment of the desired cells and depletion of contaminating tumor cells. The collected cells are stored frozen in a suitable cryoprotectant (e.g. dimethyl sulfoxide, hydroxyethyl starch) until needed. Marrow cells are collected from donors by bone puncture under anesthesia. To reduce the volume, the collected marrow is usually processed to separate plasma from the cellular components. Removal of plasma can also eliminate red cell incompatibilities in allogeneic transplantation. The cell fraction can be enriched for mononuclear cells using density gradient techniques or automated separation methods and depleted of T cells using various cytotoxic agents. Collected marrow cells are cryopreserved according to established procedures that include controlled-rate freezing and the use of cryoprotectants. Stem cells are thawed in a warm water bath immediately prior to use to minimize loss associated with thawing. In the case of allogeneic transplants, donors and recipients are tissue matched to minimize the risk of graft-versus-host disease.

An increase in hematopoietic cells results from transplantation into a recipient patient of stem cells, particularly cells of the myeloid lineage, including CD34+ stem cells and cells derived from CD34+ stem cells. Of particular interest are cells in the megakaryocyte and erythrocyte lineages, which reconstitute the recipient's platelet and erythrocyte populations, respectively.

In one aspect of the invention, a donor is treated, prior to donation of marrow or peripheral blood cells, with a compound that inhibits 2777, in an amount sufficient to stimulate proliferation of hematopoietic cells and/or in an amount sufficient to inhibit apoptosis of hematopoietic cells. Treatment of the donor will be carried out for a period of from one to several days, preferably about 2–5 days, during a period of from 3 days to 2 weeks prior to harvesting of bone marrow or peripheral blood stem cells. It is preferred to treat the donor during a period of five to ten days prior to harvesting of cells. The increase in CD34+ stem cells and other cells of the myeloid lineage in the donor will be manifested by improved recovery of hematopoietic cells in the transplant recipient. In another aspect of the invention, the recipient is treated with a compound that inhibits 2777 after transplantation to further enhance hematopoietic cell recovery.

Another aspect of the invention features a method for increasing the number of hematopoietic cells in a subject, for example, a subject undergoing radiation therapy and/or chemotherapy, e.g., for the treatment of cancer. The method includes the process of removing cells from a donor and subsequently administering the cells to a recipient. In one aspect of the invention, a donor is treated, prior to donation of marrow or peripheral blood cells, with a compound that inhibits 2777, in an amount sufficient to stimulate proliferation of hematopoietic cells and/or in an amount sufficient to inhibit apoptosis of hematopoietic cells. In another aspect of the invention, the recipient is treated with a compound that inhibits 2777 after transplantation to further enhance hematopoietic cell recovery.

In another aspect, the invention provides methods for increasing hematopoietic progenitor and committed erythroid cells in a recipient subject in need of such an increase. The methods include administering to a donor subject an amount of 2777 sufficient to inhibit induction of apoptosis and prevent inhibition of cell proliferation of hematopoietic cells in the donor; collecting cells from the donor, wherein the cells are bone marrow cells or peripheral blood stem cells; and administering the bone marrow cells or peripheral blood stem cells to a recipient subject. The donor and recipient may be different or the same subject. In one embodiment of the invention, the recipient subject has been treated with chemotherapy or radiation therapy.

In another aspect, the invention provides methods of preparing cells for transplantation comprising administering to a donor subject an amount of 2777 or a 2777 modulator sufficient to inhibit induction of apoptosis and prevent inhibition of cell proliferation of hematopoietic cells in the donor subject, and collecting cells from the donor subject, e.g., bone marrow cells or peripheral blood stem cells.

In another aspect, the invention provides a method of stimulating platelet recovery or erythrocyte recovery in a subject receiving chemotherapy or radiation therapy. The method includes administering to the subject an amount of 2777 or a 2777 modulator sufficient to stimulate proliferation of cells of the myeloid lineage in the subject; collecting bone marrow cells or peripheral blood stem cells from the subject prior to chemotherapy or radiation therapy; and returning the collected cells to the subject subsequent to chemotherapy or radiation therapy. Within one embodiment this method further includes administering to the subject, after or concurrently with returning the collected cells, an amount of 2777 or a 2777 modulator sufficient to enhance platelet recovery or erythrocyte recovery.

C. Pharmacogenomics

In conjunction with the therapeutic methods of the invention, pharmacogenomics (i.e., the study of the relationship between a subject's genotype and that subject's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an agent which modulates 2777 activity, as well as tailoring the dosage and/or therapeutic regimen of treatment with an agent which modulates 2777 activity.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate aminopeptidase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug target is known (e.g., a 2777 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and the cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., a 2777 molecule or 2777 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of a subject. This knowledge, when applied to dosing or drug selection, can avoid adverse reactions or therapeutic failure and, thus, enhance therapeutic or prophylactic efficiency when treating a subject suffering from a hematological disorder with an agent which modulates 2777 activity.

IV. Recombinant Expression Vectors and Host Cells Used in the Methods of the Invention The methods of the invention (e.g., the screening assays described herein) include the use of vectors, preferably expression vectors, containing a nucleic acid encoding a 2777 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors to be used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3–7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., 2777 proteins, mutant forms of 2777 proteins, fusion proteins, and the like).

The recombinant expression vectors to be used in the methods of the invention can be designed for expression of 2777 proteins in prokaryotic or eukaryotic cells. For example, 2777 proteins can be expressed in bacterial cells such as *E. coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in 2777 activity assays, (e.g., direct assays or competitive assays described in detail below), or to generate antibodies specific for 2777 proteins. In a preferred embodiment, a 2777 fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

In another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., *Molecular Cloning: A Laboratory Manual.* 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid).

The methods of the invention may further use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to 2777 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, *Reviews—Trends in Genetics*, Vol. 1(1) 1986.

Another aspect of the invention pertains to the use of host cells into which a 2777 nucleic acid molecule of the invention is introduced, e.g., a 2777 nucleic acid molecule within a recombinant expression vector or a 2777 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 2777 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

A host cell used in the methods of the invention, such as a prokaryotic or eukaryotic host cell in culture, can be used to produce (i.e., express) a 2777 protein. Accordingly, the invention further provides methods for producing a 2777 protein using the host cells of the invention. In one embodiment, the method comprises culturing the host cell of the invention (into which a recombinant expression vector encoding a 2777 protein has been introduced) in a suitable medium such that a 2777 protein is produced. In another embodiment, the method further comprises isolating a 2777 protein from the medium or the host cell.

V. Isolated Nucleic Acid Molecules Used in the Methods of the Invention

The coding sequence of the isolated human 2777 cDNA and the predicted amino acid sequence of the human 2777 polypeptide are shown in SEQ ID NOs:1 and 2, respectively. The amino acid sequence of the isolated human 2777 polypeptide can also be found at GenBank Accession No. P52888.

The methods of the invention include the use of isolated nucleic acid molecules that encode 2777 proteins or biologically active portions thereof, as well as nucleic acid fragments sufficient for use as hybridization probes to identify 2777-encoding nucleic acid molecules (e.g., 2777 mRNA) and fragments for use as PCR primers for the amplification or mutation of 2777 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule used in the methods of the present invention, e.g., a nucleic acid molecule having the nucleotide sequence of SEQ ID NO:1, or a portion thereof, can be isolated using standard molecular biology techniques and the sequence information provided herein. Using all or portion of the nucleic acid sequence of SEQ ID NO:1 as a hybridization probe, 2777 nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1 can be isolated by the polymerase chain reaction (PCR) using synthetic oligonucleotide primers designed based upon the sequence of SEQ ID NO:1.

A nucleic acid used in the methods of the invention can be amplified using cDNA, mRNA or, alternatively, genomic DNA as a template and appropriate oligonucleotide primers according to standard PCR amplification techniques. Furthermore, oligonucleotides corresponding to 2777 nucleotide sequences can be prepared by standard synthetic techniques, e.g., using an automated DNA synthesizer.

In a preferred embodiment, the isolated nucleic acid molecules used in the methods of the invention comprise the nucleotide sequence shown in SEQ ID NO:1, a complement of the nucleotide sequence shown in SEQ ID NO:1, or a portion of any of these nucleotide sequences. A nucleic acid molecule which is complementary to the nucleotide sequence shown in SEQ ID NO:1, is one which is sufficiently complementary to the nucleotide sequence shown in SEQ ID NO:1 such that it can hybridize to the nucleotide sequence shown in SEQ ID NO:1 thereby forming a stable duplex.

In still another preferred embodiment, an isolated nucleic acid molecule used in the methods of the present invention comprises a nucleotide sequence which is at least about 55%, 60%, 65%, 70%, 75%, 80%, 85%, 90%, 95%, 96%, 97%, 98%, 99% or more identical to the entire length of the nucleotide sequence shown in SEQ ID NO:1 or a portion of any of this nucleotide sequence.

Moreover, the nucleic acid molecules used in the methods of the invention can comprise only a portion of the nucleic acid sequence of SEQ ID NO:1, for example, a fragment which can be used as a probe or primer or a fragment encoding a portion of a 2777 protein, e.g., a biologically active portion of a 2777 protein. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 of an anti-sense sequence of SEQ ID NO:1 or of a naturally occurring allelic variant or mutant of SEQ ID NO:1. In one embodiment, a nucleic acid molecule used in the methods of the present invention comprises a nucleotide sequence which is greater than 100, 100–200, 200–300, 300–400, 400–500, 500–600, or more nucleotides in length and hybridizes under stringent hybridization conditions to a nucleic acid molecule of SEQ ID NO:1.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\% \text{ G+C})-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5 M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991–1995, (or alternatively 0.2×SSC, 1% SDS).

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a 2777 protein, such as by measuring a level of a 2777-encoding nucleic acid in a sample of cells from a subject e.g., detecting 2777 mRNA levels or determining whether a genomic 2777 gene has been mutated or deleted.

The methods of the invention further encompass the use of nucleic acid molecules that differ from the nucleotide sequence shown in SEQ ID NO:1 due to degeneracy of the genetic code and thus encode the same 2777 proteins as those encoded by the nucleotide sequence shown in SEQ ID NO:1. In another embodiment, an isolated nucleic acid molecule included in the methods of the invention has a nucleotide sequence encoding a protein having an amino acid sequence shown in SEQ ID NO:2.

The methods of the invention further include the use of allelic variants of human 2777, e.g., fuctional and non-functional allelic variants. Functional allelic variants are naturally occurring amino acid sequence variants of the human 2777 protein that maintain a 2777 activity. Functional allelic variants will typically contain only conservative substitution of one or more amino acids of SEQ ID NO:2, or substitution, deletion or insertion of non-critical residues in non-critical regions of the protein. Non-functional allelic variants are naturally occurring amino acid sequence variants of the human 2777 protein that do not have a 2777 activity. Non-functional allelic variants will typically contain a non-conservative substitution, deletion, or insertion or premature truncation of the amino acid sequence of SEQ ID NO:2, or a substitution, insertion or deletion in critical residues or critical regions of the protein.

The methods of the present invention may further use non-human orthologues of the human 2777 protein. Orthologues of the human 2777 protein are proteins that are isolated from non-human organisms and possess the same 2777 activity.

The methods of the present invention further include the use of nucleic acid molecules comprising the nucleotide sequence of SEQ ID NO:1 or a portion thereof, in which a mutation has been introduced. The mutation may lead to amino acid substitutions at "non-essential" amino acid residues or at "essential" amino acid residues. A "non-essential" amino acid residue is a residue that can be altered from the wild-type sequence of 2777 (e.g., the sequence of SEQ ID NO:2) without altering the biological activity, whereas an "essential" amino acid residue is required for biological activity. For example, amino acid residues that are conserved among the 2777 proteins of the present invention and other members of the CIDE family (e.g., CIDE-B, FSP-27, and DFF45) are not likely to be amenable to alteration.

Mutations can be introduced into SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a 2777 protein is preferably replaced with another amino acid residue from the same side chain family. Alternatively, in another embodiment, mutations can be introduced randomly along all or part of a 2777 coding sequence, such as by saturation mutagenesis, and the resultant mutants can be screened for 2777 biological activity to identify mutants that retain activity. Following mutagenesis of SEQ ID NO:1 the encoded protein can be expressed recombinantly and the activity of the protein can be determined using the assay described herein.

Another aspect of the invention pertains to the use of isolated nucleic acid molecules which are antisense to the nucleotide sequence of SEQ ID NO:1. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire 2777 coding strand, or to only a portion thereof. In one embodiment, an antisense nucleic acid molecule is antisense to a "coding region" of the coding strand of a nucleotide sequence encoding a 2777. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding 2777. The term "noncoding region" refers to 5' and 3' sequences which flank the coding region that are not translated into amino acids (also referred to as 5' and 3' untranslated regions).

Given the coding strand sequences encoding 2777 disclosed herein, antisense nucleic acids of the invention can be designed according to the rules of Watson and Crick base pairing. The antisense nucleic acid molecule can be complementary to the entire coding region of 2777 mRNA, but more preferably is an oligonucleotide which is antisense to only a portion of the coding or noncoding region of 2777 mRNA. For example, the antisense oligonucleotide can be complementary to the region surrounding the translation start site of 2777 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules used in the methods of the invention are typically administered to a subject or generated in situ such that they hybridize with or bind to cellular mRNA and/or genomic DNA encoding a 2777 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule used in the methods of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

In still another embodiment, an antisense nucleic acid used in the methods of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave 2777 mRNA transcripts to thereby inhibit translation of 2777 mRNA. A ribozyme having specificity for a 2777-encoding nucleic acid can be designed based upon the nucleotide sequence of a 2777 cDNA disclosed herein (i.e., SEQ ID NO:1). For example, a derivative of a *Tetrahymena* L-19 IVS RNA can be constructed in which the nucleotide sequence of the active site is complementary to the nucleotide sequence to be cleaved in a 2777-encoding mRNA. See, e.g., Cech et al. U.S. Pat. No. 4,987,071; and Cech et al. U.S. Pat. No. 5,116,742. Alternatively, 2777 mRNA can be used to select a catalytic RNA having a specific ribonuclease activity from a pool of RNA molecules. See, e.g., Bartel, D. and Szostak, J. W. (1993) *Science* 261:1411–1418.

Alternatively, 2777 gene expression can be inhibited by targeting nucleotide sequences complementary to the regulatory region of the 2777 (e.g., the 2777 promoter and/or enhancers) to form triple helical structures that prevent transcription of the 2777 gene in target cells. See generally, Helene, C. (1991) *Anticancer Drug Des.* 6(6): 569–84; Helene, C. et al. (1992) *Ann. N.Y. Acad. Sci.* 660:27–36; and Maher, L. J. (1992) *Bioassays* 14(12):807–15.

In yet another embodiment, the 2777 nucleic acid molecules used in the methods of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. (1996) *Proc. Natl. Acad. Sci.* 93:14670–675.

PNAs of 2777 nucleic acid molecules can be used in the therapeutic and diagnostic applications described herein. For example, PNAs can be used as antisense or antigene agents for sequence-specific modulation of gene expression by, for example, inducing transcription or translation arrest or inhibiting replication. PNAs of 2777 nucleic acid molecules can also be used in the analysis of single base pair mutations in a gene, (e.g., by PNA-directed PCR clamping); as 'artificial restriction enzymes' when used, in combination with other enzymes, (e.g., S1 nucleases (Hyrup B. et al. (1996) supra)); or as probes or primers for DNA sequencing or hybridization (Hyrup B. et al. (1996) supra; Perry-O'Keefe et al. (1996) supra).

In another embodiment, PNAs of 2777 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of 2777 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. et al. (1996) supra). The synthesis of PNA-DNA chimeras can be performed as described in Hyrup B. et al. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide used in the methods of the invention may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958–976) or intercalating agents. (See, e.g., Zon (1988)

*Pharm. Res.* 5:539–549). To this end, the oligonucleotide may be conjugated to another molecule, (e.g., a peptide, hybridization triggered cross-linking agent, transport agent, or hybridization-triggered cleavage agent).

VI. Isolated 2777 Proteins and Anti-2777 Antibodies Used in the Methods of the Invention The methods of the invention include the use of isolated 2777 proteins, and biologically active portions thereof, as well as polypeptide fragments suitable for use as immunogens to raise anti-2777 antibodies. In one embodiment, native 2777 proteins can be isolated from cells or tissue sources by an appropriate purification scheme using standard protein purification techniques. In another embodiment, 2777 proteins are produced by recombinant DNA techniques. Alternative to recombinant expression, a 2777 protein or polypeptide can be synthesized chemically using standard peptide synthesis techniques.

As used herein, a "biologically active portion" of a 2777 protein includes a fragment of a 2777 protein having a 2777 activity. Biologically active portions of a 2777 protein include peptides comprising amino acid sequences sufficiently identical to or derived from the amino acid sequence of the 2777 protein, e.g., the amino acid sequence shown in SEQ ID NO:2, which include fewer amino acids than the full length 2777 proteins, and exhibit at least one activity of a 2777 protein. Typically, biologically active portions comprise a domain or motif with at least one activity of the 2777 protein (e.g., the N-terminal region of the 2777 protein that is believed to be involved in the regulation of apoptotic activity). A biologically active portion of a 2777 protein can be a polypeptide which is, for example, 25, 50, 75, 100, 125, 150, 175, 200, 250, 300 or more amino acids in length. Biologically active portions of a 2777 protein can be used as targets for developing agents which modulate a 2777 activity.

In a preferred embodiment, the 2777 protein used in the methods of the invention has an amino acid sequence shown in SEQ ID NO:2. In other embodiments, the 2777 protein is substantially identical to SEQ ID NO:2, and retains the functional activity of the protein of SEQ ID NO:2, yet differs in amino acid sequence due to natural allelic variation or mutagenesis, as described in detail in subsection V above. Accordingly, in another embodiment, the 2777 protein used in the methods of the invention is a protein which comprises an amino acid sequence at least about 50%, 55%, 60%, 65%, 70%, 75%, 80%, 85%, 90%, 95%, 96%, 97%, 98%, 99% or more identical to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the 2777 amino acid sequence of SEQ ID NO:2 having 500 amino acid residues, at least 75, preferably at least 150, more preferably at least 225, even more preferably at least 300, and even more preferably at least 400 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444–453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.* 4:11–17 (1988)) which has been incorporated into the ALIGN program (version 2.0 or 20.U), using a PAM120 weight residue table, a gap length penalty of 12 and a gap penalty of 4.

The methods of the invention may also use 2777 chimeric or fusion proteins. As used herein, a 2777 "chimeric protein" or "fusion protein" comprises a 2777 polypeptide operatively linked to a non-2777 polypeptide. An "2777 polypeptide" refers to a polypeptide having an amino acid sequence corresponding to a 2777 molecule, whereas a "non-2777 polypeptide" refers to a polypeptide having an amino acid sequence corresponding to a protein which is not substantially homologous to the 2777 protein, e.g., a protein which is different from the 2777 protein and which is derived from the same or a different organism. Within a 2777 fusion protein the 2777 polypeptide can correspond to all or a portion of a 2777 protein. In a preferred embodiment, a 2777 fusion protein comprises at least one biologically active portion of a 2777 protein. In another preferred embodiment, a 2777 fusion protein comprises at least two biologically active portions of a 2777 protein. Within the fusion protein, the term "operatively linked" is intended to indicate that the 2777 polypeptide and the non-2777 polypeptide are fused in-frame to each other. The non-2777 polypeptide can be fused to the N-terminus or C-terminus of the 2777 polypeptide.

For example, in one embodiment, the fusion protein is a GST-2777 fusion protein in which the 2777 sequences are fused to the C-terminus of the GST sequences. Such fusion proteins can facilitate the purification of recombinant 2777.

In another embodiment, this fusion protein is a 2777 protein containing a heterologous signal sequence at its N-terminus. In certain host cells (e.g., mammalian host cells), expression and/or secretion of 2777 can be increased through use of a heterologous signal sequence.

The 2777 fusion proteins used in the methods of the invention can be incorporated into pharmaceutical compositions and administered to a subject in vivo. The 2777 fusion proteins can be used to affect the bioavailability of a 2777 substrate. Use of 2777 fusion proteins may be useful therapeutically for the treatment of disorders caused by, for example, (i) aberrant modification or mutation of a gene encoding a 2777 protein; (ii) mis-regulation of the 2777 gene; and (iii) aberrant post-translational modification of a 2777 protein.

Moreover, the 2777-fusion proteins used in the methods of the invention can be used as immunogens to produce anti-2777 antibodies in a subject, to purify 2777 ligands and in screening assays to identify molecules which inhibit the interaction of 2777 with a 2777 substrate.

Preferably, a 2777 chimeric or fusion protein used in the methods of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A 2777-encoding nucleic acid can be cloned into such an expression vector such that the fusion moiety is linked in-frame to the 2777 protein.

The present invention also pertains to the use of variants of the 2777 proteins which function as either 2777 agonists (mimetics) or as 2777 antagonists. Variants of the 2777 proteins can be generated by mutagenesis, e.g., discrete point mutation or truncation of a 2777 protein. An agonist of the 2777 proteins can retain substantially the same, or a subset, of the biological activities of the naturally occurring form of a 2777 protein. An antagonist of a 2777 protein can inhibit one or more of the activities of the naturally occurring form of the 2777 protein by, for example, competitively modulating a 2777-mediated activity of a 2777 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the 2777 protein.

In one embodiment, variants of a 2777 protein which function as either 2777 agonists (mimetics) or as 2777 antagonists can be identified by screening combinatorial libraries of mutants, e.g., truncation mutants, of a 2777 protein for 2777 protein agonist or antagonist activity. In one embodiment, a variegated library of 2777 variants is generated by combinatorial mutagenesis at the nucleic acid level and is encoded by a variegated gene library. A variegated library of 2777 variants can be produced by, for example, enzymatically ligating a mixture of synthetic oligonucleotides into gene sequences such that a degenerate set of potential 2777 sequences is expressible as individual polypeptides, or alternatively, as a set of larger fusion proteins (e.g., for phage display) containing the set of 2777 sequences therein. There are a variety of methods which can be used to produce libraries of potential 2777 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential 2777 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a 2777 protein coding sequence can be used to generate a variegated population of 2777 fragments for screening and subsequent selection of variants of a 2777 protein. In one embodiment, a library of coding sequence fragments can be generated by treating a double stranded PCR fragment of a 2777 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the 2777 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of 2777 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify 2777 variants (Arkin and Yourvan (1992) *Proc. Natl. Acad. Sci. USA* 89:7811–7815; Delgrave et al. (1993) *Protein Engineering* 6(3):327–331).

The methods of the present invention further include the use of anti-2777 antibodies. An isolated 2777 protein, or a portion or fragment thereof, can be used as an immunogen to generate antibodies that bind 2777 using standard techniques for polyclonal and monoclonal antibody preparation. A full-length 2777 protein can be used or, alternatively, antigenic peptide fragments of 2777 can be used as immunogens. The antigenic peptide of 2777 comprises at least 8 amino acid residues of the amino acid sequence shown in SEQ ID NO:2 and encompasses an epitope of 2777 such that an antibody raised against the peptide forms a specific immune complex with the 2777 protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of 2777 that are located on the surface of the protein, e.g., hydrophilic regions, as well as regions with high antigenicity.

A 2777 immunogen is typically used to prepare antibodies by immunizing a suitable subject, (e.g., rabbit, goat, mouse, or other mammal) with the immunogen. An appropriate immunogenic preparation can contain, for example, recombinantly expressed 2777 protein or a chemically synthesized 2777 polypeptide. The preparation can further include an adjuvant, such as Freund's complete or incomplete adjuvant, or similar immunostimulatory agent. Immunization of a suitable subject with an immunogenic 2777 preparation induces a polyclonal anti-2777 antibody response.

The term "antibody" as used herein refers to immunoglobulin molecules and immunologically active portions of immunoglobulin molecules, i.e., molecules that contain an antigen binding site which specifically binds (immunoreacts with) an antigen, such as a 2777. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind 2777 molecules. The term "monoclonal antibody" or "monoclonal antibody composition", as used herein, refers to a population of antibody molecules that contain only one species of an antigen binding site capable of immunoreacting with a particular epitope of 2777. A monoclonal antibody composition thus typically displays a single binding affinity for a particular 2777 protein with which it immunoreacts.

Polyclonal anti-2777 antibodies can be prepared as described above by immunizing a suitable subject with a 2777 immunogen. The anti-2777 antibody titer in the immunized subject can be monitored over time by standard techniques, such as with an enzyme linked immunosorbent assay (ELISA) using immobilized 2777. If desired, the antibody molecules directed against 2777 can be isolated from the mammal (e.g., from the blood) and further purified by well known techniques, such as protein A chromatography to obtain the IgG fraction. At an appropriate time after immunization, e.g., when the anti-2777 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985) *Monoclonal Antibodies and Cancer Therapy*, Alan R. Liss, Inc., pp. 77–96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387–402; Gefter, M. L. et al. (1977) *Somatic Cell Genet.* 3:231–36). Briefly, an immortal cell line (typically a myeloma) is fused to lymphocytes (typically splenocytes) from a mammal immunized with a 2777 immunogen as described above, and the culture supernatants of the resulting hybridoma cells are screened to identify a hybridoma producing a monoclonal antibody that binds 2777.

Any of the many well known protocols used for fusing lymphocytes and immortalized cell lines can be applied for the purpose of generating an anti-2777 monoclonal antibody (see, e.g., G. Galfre et al. (1977) *Nature* 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind 2777, e.g., using a standard ELISA assay.

Alternative to preparing monoclonal antibody-secreting hybridomas, a monoclonal anti-2777 antibody can be identified and isolated by screening a recombinant combinatorial immunoglobulin library (e.g., an antibody phage display library) with 2777 to thereby isolate immunoglobulin library members that bind 2777. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. (1990) *Nature* 348:552–554.

Additionally, recombinant anti-2777 antibodies, such as chimeric and humanized monoclonal antibodies, comprising both human and non-human portions, which can be made using standard recombinant DNA techniques, are within the scope of the methods of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125, 023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559; Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-2777 antibody can be used to detect 2777 protein (e.g., in a cellular lysate or cell supernatant) in order to evaluate the abundance and pattern of expression of the 2777 protein. Anti-2777 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, □-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

VII. Electronic Apparatus Readable Media and Arrays

Electronic apparatus readable media comprising a 2777 modulator of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 2777 modulators of the present invention.

A variety of software programs and formats can be used to store the marker information of the present invention on the electronic apparatus readable medium. For example, the nucleic acid sequence corresponding to the 2777 modulators can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of dataprocessor structuring formats (e.g., text file or database) may be employed in order to obtain or create a medium having recorded thereon the 2777 modulators of the present invention.

By providing the 2777 modulators of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a hematological disorder or a pre-disposition to a hematological disroder, wherein the method comprises the steps of determining the presence or absence of a 2777 modulator and based on the presence or absence of the 2777 modulator, determining whether the subject has a hematological disorder or a pre-disposition to a hematological disorder and/or recommending a particular treatment for the hematological disorder or pre-hematological disorder condition.

The present invention further provides in an electronic system and/or in a network, a method for determining whether a subject has a hematological disorder or a pre-disposition to a hematological disorder associated with a 2777 modulator wherein the method comprises the steps of determining the presence or absence of the 2777 modulator, and based on the presence or absence of the 2777 modulator, determining whether the subject has a hematological disorder or a pre-disposition to a hematological disorder, and/or recommending a particular treatment for the hematological disorder or pre-hematological disorder condition. The method may further comprise the step of receiving phenotypic information associated with the subject and/or acquiring from a network phenotypic information associated with the subject.

The present invention also provides in a network, a method for determining whether a subject has a hematological disorder or a pre-disposition to a hematological disorder associated with a 2777 modulator, said method comprising the steps of receiving information associated with the 2777 modulator receiving phenotypic information associated with the subject, acquiring information from the network corresponding to the 2777 modulator and/or hematological disorder, and based on one or more of the phenotypic information, the 2777 modulator, and the acquired information, determining whether the subject has a hematological disorder or a pre-disposition to a hematological disorder. The method may further comprise the step of recommending a particular treatment for the hematological disorder or pre- hematological disorder condition.

The present invention also provides a business method for determining whether a subject has a hematological disorder or a pre-disposition to a hematological disorder, said method comprising the steps of receiving information associated with the 2777 modulator, receiving phenotypic information associated with the subject, acquiring information from the network corresponding to the 2777 modulator and/or hematological disorder, and based on one or more of the phenotypic information, the 2777 modulator, and the acquired information, determining whether the subject has a hematological disorder or a pre-disposition to a hematological disorder. The method may further comprise the step of recommending a particular treatment for the hematological disorder or pre-hematological disorder condition.

The invention also includes an array comprising a 2777 modulator of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of hematological disorder, progression of hematological disorder, and processes, such a cellular transformation associated with hematological disorder.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

This invention is further illustrated by the following examples which should not be construed as limiting. The contents of all references, patents and published patent applications cited throughout this application, as well as the Figure and the Sequence Listing is incorporated herein by reference.

EXAMPLES

Example 1

Identification of 2777 as a Modulator of Hematological Disorders

This example describes the distribution of 2777 in normal tissue derived from a variety of organs and, in particular, hematopoietic cells during various points of cell differentiation.

Materials and Methods

For analysis of human and murine 2777 expression in hematopoietic cells and tissue, the following methods were used:

Tissues were collected from 7 week old female C57/B16J mice. Total RNA was prepared using the trizol method and treated with DNAse to remove contaminating genomic DNA. cDNA was synthesized using standard techniques. Mock cDNA synthesis in the absence of reverse transcriptase resulted in samples with no detectable PCR amplification of the control RNA gene confirming efficient removal of genomic DNA contamination. 2777 expression was measured by TaqMan® quantitative PCR analysis, performed according to the manufacturer's directions (Perkin Elmer Applied Biosystems, Foster City, Calif.).

The samples included the following normal cells and tissues: heart, brain, lung, liver, fetal liver, spleen, kidney, CD3 (T cells), CD4, CD8, CD 14, bone marrow, CD34, cord blodd, GPA-hi, GPA-lo, pooled neutorphils, pooled megakaryocytes, K562 (leukemia cells), stromal, Human Endothelial Cells ("HUVEC"), HCAEC (human coronary artery endothelial cells), skeletal muscle, small intestine, pancreas, sinal cord, breast, ovary, prostate, erythroid, macrophages and lymph node (see FIG. 1).

PCR probes were designed by PrimerExpress software (PE Biosystems) based on the sequence of human 2777 (SEQ ID NO:1).

To standardize the results between different tissues, two probes, distinguished by different fluorescent labels, were added to each sample. The differential labeling of the probe for the 2777 gene and the probe for control RNA as an internal control thus enabled their simultaneous measurement in the same well. Forward and reverse primers and the probes for both control RNA and human 2777 were added to the TaqMan Universal PCR Master Mix (PE Applied Biosystems). Although the final concentration of primer and probe could vary, each was internally consistent within a given experiment. A typical experiment contained 200 nM of forward and reverse primers, plus 100 nM of the probe for the control RNA, and 4500 nM of each of the forward and reverse primers, plus 150 nM of the probe for murine 2777-2. TaqMan matrix experiments were carried out using an ABI PRISM 770 Sequence Detection System (PE Applied Biosystems). The thermal cycler conditions were as follows: hold for 2 minutes at 50° C. and 10 minutes at 95° C., followed by two-step PCR for 40 cycles of 95° C. for 15 seconds, followed by 60° C. for 1 minute.

The following method was used to quantitatively calculate 2777 gene expression in the tissue samples, relative to the control RNA expression in the same tissue. The threshold values at which the PCR amplification started were determined using the manufacturer's software. PCR cycle number at threshold value was designated as CT. Relative expression was calculated as:

$$2^{-((CTtest-CT18S)tissue\ of\ interest-(CTtest-CT18S)lowest\ expressing\ tissue\ in\ panel)}$$

Samples were run in duplicate and the averages of 2 relative expression determinations are shown. All probes were tested on serial dilutions of RNA from a tissue with high expression levels and only probes which gave relative expression levels that were linear to the amount of template cDNA with a slope similar to the slope for the internal control 18S were used.

For Northern Blotting, human mRNA blots (Clontech) were probed with a 520 nucleotide SacI fragment containing 420 nucleotides of the 5' coding sequence and 100 nucleotides of the 5' UTR of human 2777. Probes were labeled with $^{32}P$ and hybridized using the Rapid-Hyb buffer (Amersham).

Results

The expression of 2777 was examined in various tissues and in hematopoietic cells both in vitro and in vivo. As shown in FIG. 1, the results of the foregoing experiments indicate that 2777 is highly expressed in cells of the erythroid lineage both in vivo and in vitro. Specifically, erythroid cultures showed increasing levels of expression up to Day 6 of differentiation. 2777 was also highly expressed in BFU-E cells and in GPA-lo cells but expressed in low levels in GPA-hi cells in vivo. In organ recitals, 2777 was expressed at high levels in brain, HUVEC cells and erythroid cells. To verify expression of 2777, Northern Blotting was performed using commercially available Clontech Blots.

The results described above demonstrate that 2777 is expressed in hematopoietic cells. Thus, 2777 may play an important role in modulating peptide hormones which stimulate erythropoiesis.

Equivalents

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 3

<210> SEQ ID NO 1
<211> LENGTH: 2515
<212> TYPE: DNA
<213> ORGANISM: Homo sapien

<400> SEQUENCE: 1

```
gaattccggg gcatgctgtg gcggcggttg ggccgaggca ggcggcctca gtggccgagg      60
tggcttggac gcgtacgagg tggaaggagg gagggagccg caggcgcaga cccacagacc     120
acccgccatg aagcccccg cagcctgtgc aggagacatg gcggacgcag catctccgtg     180
ctctgtggta aacgacctgc ggtgggacct gagtgcccag cagatagagg agcgcaccag     240
ggagctcatc gagcagacca agcgcgtgta tgaccaggtt ggcacccagg agtttgagga     300
cgtgtcctac gagagcacgc tcaaggcgct ggccgatgtg gaggtcacct acacagttca     360
gaggaatatc cttgacttcc cccagcatgt ttccccctcc aaggacatcc ggacagccag     420
cacagaggcc gacaagaagc tctctgagtt cgacgtggag atgagcatga gggaggacgt     480
gtaccagagg atcgtgtggc tccaggagaa agttcagaag gactcactga ggcccgaggc     540
tgcgcggtac ctggagcggc taatcaagct gggccggaga aatgggcttc acctccccag     600
agagactcag gaaaacatca aacgcatcaa gaagaagctg agccttctgt gcatcgactt     660
caacaagaac ctgaacgagg acacgacctt cctgcccttc acgctccagg agctaggagg     720
gctccccgag gactttctga actccctgga gaagatggag gacggcaagt tgaaggtcac     780
cctcaagtac ccccattact tcccctcct gaagaaatgc cacgtgcctg agaccaggag     840
gaaagtggag gaggccttca actgccggtg caaggaggag aactgcgcta tcctcaagga     900
gctggtgacg ctgcgggccc agaagtcccg cctgctgggg ttccacacgc acgccgacta     960
tgtcctggag atgaacatgg ccaagaccag ccagaccgtg gccaccttcc tagatgagct    1020
ggcgcagaag ctgaagcccc tgggggagca ggagcgtgcg gtgattctgg agctgaagcg    1080
tgcggagtgc gagcgccggg gcctgccctt cgacggccgc atccgtgcct gggacatgcg    1140
```

-continued

```
ctactacatg aaccaggtgg aggagacgcg ctactgcgtg gaccagaacc tgctcaagga    1200
gtacttcccc gtgcaggtgg tcacgcacgg gctgctgggc atctaccagg agctcctggg    1260
gctggccttc caccacgagg agggcgccag tgcctggcat gaggacgtgc ggctctacac    1320
cgcgagggac gcggcctcgg gggaggtggt cggcaagttc tacctggacc tgtacccgcg    1380
ggaaggaaag tacgggcacg cggcctgctt tggcctgcag cccggctgcc tgcggcagga    1440
tgggagccgc cagatcgcca tcgcggccat ggtggccaac ttcaccaagc ccacagccga    1500
cgcgccctcg ctgctgcagc atgacgaggt ggagacctac ttccatgagt ttggccacgt    1560
gatgcaccag ctctgctccc aggcggagtt cgccatgttc agcgggaccc acgtggagcg    1620
ggactttgtg gaggcgccgt cgcagatgct ggagaactgg gtgtgggagc aggagccgct    1680
gctgcggatg tcgcggcact accgcacagg cagcgccgtg ccccgggagc tcctggagaa    1740
gctcattgag tcccggcagg ccaacacagg cctcttcaac ctgcgccaga tcgtcctcgc    1800
caaggtggac caggccctgc acacgcagac ggacgcagac cccgccgagg agtatgcgcg    1860
gctctgccag gagatcctcg gggtcccggc cacgccagga accaacatgc ctgcaacctt    1920
cggccatctg gcaggtggct acgacgccca gtactacggg tacctgtgga gcgaggtgta    1980
ttccatggac atgttccaca cgcgcttcaa gcaggagggt gtcctgaaca gcaaggttgg    2040
catggattac agaagctgca tcctgagacc cggcggttcc gaggatgcca gcgccatgct    2100
gaggcgcttc ctgggccgtg accccaagca ggacgccttc ctcctgagca aggggctgca    2160
ggtcgggggc tgcgagcccg agccgcaggt ctgctgaggc ctggcactgc gactgcccag    2220
tctggcctgc gctcccgccg ccctggtgcc ttagcccccg gcacaggatg gggcaagctc    2280
tggcacagtg ccttgggact ggactggcag ggtggctgag cggctgtctt gcctcttgtc    2340
attgtctgtc cccacccggt cgtggcccac ccggctagac ggcgtcctca aggcatctgg    2400
agggctttcg tggctgccag ggcctggtct tgttgcact aacacgtctc ctctctggga    2460 aacgtcccctt gtcaggagac ggctcttctt tgaaatgagg tcattaaaag gaaac        2515
```

<210> SEQ ID NO 2
<211> LENGTH: 836
<212> TYPE: PRT
<213> ORGANISM: Homo sapien

<400> SEQUENCE: 2

```
Asn Ser Gly Ala Cys Cys Gly Gly Gly Trp Ala Glu Ala Gly Gly Leu
  1               5                  10                  15

Ser Gly Arg Gly Gly Leu Asp Ala Tyr Glu Val Glu Gly Gly Arg Glu
                 20                  25                  30

Pro Gln Ala Gln Thr His Arg Pro Ala Met Lys Pro Ala Ala
             35                  40                  45

Cys Ala Gly Asp Met Ala Asp Ala Ala Ser Pro Cys Ser Val Val Asn
         50                  55                  60

Asp Leu Arg Trp Asp Leu Ser Ala Gln Gln Ile Glu Glu Arg Thr Arg
 65                  70                  75                  80

Glu Leu Ile Glu Gln Thr Lys Arg Val Tyr Asp Gln Val Gly Thr Gln
                 85                  90                  95

Glu Phe Glu Asp Val Ser Tyr Glu Ser Thr Leu Lys Ala Leu Ala Asp
                100                 105                 110

Val Glu Val Thr Tyr Thr Val Gln Arg Asn Ile Leu Asp Phe Pro Gln
                115                 120                 125
```

```
His Val Ser Pro Ser Lys Asp Ile Arg Thr Ala Ser Thr Glu Ala Asp
    130                 135                 140

Lys Lys Leu Ser Glu Phe Asp Val Glu Met Ser Met Arg Glu Asp Val
145                 150                 155                 160

Tyr Gln Arg Ile Val Trp Leu Gln Glu Lys Val Gln Lys Asp Ser Leu
                165                 170                 175

Arg Pro Glu Ala Ala Arg Tyr Leu Glu Arg Leu Ile Lys Leu Gly Arg
            180                 185                 190

Arg Asn Gly Leu His Leu Pro Arg Glu Thr Gln Glu Asn Ile Lys Arg
        195                 200                 205

Ile Lys Lys Lys Leu Ser Leu Leu Cys Ile Asp Phe Asn Lys Asn Leu
    210                 215                 220

Asn Glu Asp Thr Thr Phe Leu Pro Phe Thr Leu Gln Glu Leu Gly Gly
225                 230                 235                 240

Leu Pro Glu Asp Phe Leu Asn Ser Leu Glu Lys Met Glu Asp Gly Lys
                245                 250                 255

Leu Lys Val Thr Leu Lys Tyr Pro His Tyr Phe Pro Leu Leu Lys Lys
            260                 265                 270

Cys His Val Pro Glu Thr Arg Arg Lys Val Glu Glu Ala Phe Asn Cys
        275                 280                 285

Arg Cys Lys Glu Glu Asn Cys Ala Ile Leu Lys Glu Leu Val Thr Leu
    290                 295                 300

Arg Ala Gln Lys Ser Arg Leu Leu Gly Phe His Thr His Ala Asp Tyr
305                 310                 315                 320

Val Leu Glu Met Asn Met Ala Lys Thr Ser Gln Thr Val Ala Thr Phe
                325                 330                 335

Leu Asp Glu Leu Ala Gln Lys Leu Lys Pro Leu Gly Glu Gln Glu Arg
            340                 345                 350

Ala Val Ile Leu Glu Leu Lys Arg Ala Glu Cys Glu Arg Arg Gly Leu
        355                 360                 365

Pro Phe Asp Gly Arg Ile Arg Ala Trp Asp Met Arg Tyr Tyr Met Asn
    370                 375                 380

Gln Val Glu Glu Thr Arg Tyr Cys Val Asp Gln Asn Leu Leu Lys Glu
385                 390                 395                 400

Tyr Phe Pro Val Gln Val Thr His Gly Leu Leu Gly Ile Tyr Gln
                405                 410                 415

Glu Leu Leu Gly Leu Ala Phe His His Glu Glu Gly Ala Ser Ala Trp
            420                 425                 430

His Glu Asp Val Arg Leu Tyr Thr Ala Arg Asp Ala Ala Ser Gly Glu
        435                 440                 445

Val Val Gly Lys Phe Tyr Leu Asp Leu Tyr Pro Arg Glu Gly Lys Tyr
    450                 455                 460

Gly His Ala Ala Cys Phe Gly Leu Gln Pro Gly Cys Leu Arg Gln Asp
465                 470                 475                 480

Gly Ser Arg Gln Ile Ala Ile Ala Ala Met Val Ala Asn Phe Thr Lys
                485                 490                 495

Pro Thr Ala Asp Ala Pro Ser Leu Leu Gln His Asp Glu Val Glu Thr
            500                 505                 510

Tyr Phe His Glu Phe Gly His Val Met His Gln Leu Cys Ser Gln Ala
        515                 520                 525

Glu Phe Ala Met Phe Ser Gly Thr His Val Glu Arg Asp Phe Val Glu
    530                 535                 540
```

-continued

| | | | | | | | | | | | |
|---|---|---|---|---|---|---|---|---|---|---|---|
| Ala | Pro | Ser | Gln | Met | Leu | Glu | Asn | Trp | Val | Trp | Gln | Glu | Pro | Leu |
| 545 | | | | 550 | | | | | 555 | | | | | 560 |

Leu Arg Met Ser Arg His Tyr Arg Thr Gly Ser Ala Val Pro Arg Glu
            565                 570                 575

Leu Leu Glu Lys Leu Ile Glu Ser Arg Gln Ala Asn Thr Gly Leu Phe
        580                 585                 590

Asn Leu Arg Gln Ile Val Leu Ala Lys Val Asp Gln Ala Leu His Thr
    595                 600                 605

Gln Thr Asp Ala Asp Pro Ala Glu Glu Tyr Ala Arg Leu Cys Gln Glu
    610                 615                 620

Ile Leu Gly Val Pro Ala Thr Pro Gly Thr Asn Met Pro Ala Thr Phe
625                 630                 635                 640

Gly His Leu Ala Gly Gly Tyr Asp Ala Gln Tyr Tyr Gly Tyr Leu Trp
            645                 650                 655

Ser Glu Val Tyr Ser Met Asp Met Phe His Thr Arg Phe Lys Gln Glu
            660                 665                 670

Gly Val Leu Asn Ser Lys Val Gly Met Asp Tyr Arg Ser Cys Ile Leu
        675                 680                 685

Arg Pro Gly Gly Ser Glu Asp Ala Ser Ala Met Leu Arg Arg Phe Leu
    690                 695                 700

Gly Arg Asp Pro Lys Gln Asp Ala Phe Leu Leu Ser Lys Gly Leu Gln
705                 710                 715                 720

Val Gly Gly Cys Glu Pro Glu Pro Gln Val Cys Gly Leu Ala Leu Arg
            725                 730                 735

Leu Pro Ser Leu Ala Cys Ala Pro Ala Ala Leu Val Pro Pro Pro Ala
            740                 745                 750

Gln Asp Gly Ala Ser Ser Gly Thr Val Pro Trp Asp Trp Thr Gly Arg
        755                 760                 765

Val Ala Glu Arg Leu Ser Cys Leu Leu Ser Leu Ser Val Pro Thr Arg
    770                 775                 780

Ser Trp Pro Thr Arg Leu Asp Gly Val Leu Lys Ala Ser Gly Gly Leu
785                 790                 795                 800

Ser Trp Leu Pro Gly Pro Gly Leu Cys Cys Thr Asn Thr Ser Pro Leu
            805                 810                 815

Trp Glu Thr Ser Leu Val Arg Arg Arg Leu Phe Phe Glu Met Arg Ser
            820                 825                 830

Leu Lys Gly Asn
        835

<210> SEQ ID NO 3
<211> LENGTH: 2515
<212> TYPE: DNA
<213> ORGANISM: Homo sapien
<220> FEATURE:
<221> NAME/KEY: CDS
<222> LOCATION: (128)...(2197)

<400> SEQUENCE: 3
gaattccggg gcatgctgtg gcggcggttg ggccgaggca ggcggcctca gtggccgagg    60
tggcttggac gcgtacgagg tggaaggagg gagggagccg caggcgcaga cccacagacc   120 acccgcc atg aag ccc ccc gca gcc tgt gca gga gac atg gcg gac gca   169
        Met Lys Pro Pro Ala Ala Cys Ala Gly Asp Met Ala Asp Ala
          1               5                  10 gca tct ccg tgc tct gtg gta aac gac ctg cgg tgg gac ctg agt gcc   217
Ala Ser Pro Cys Ser Val Val Asn Asp Leu Arg Trp Asp Leu Ser Ala
 15              20                  25                  30

```
cag cag ata gag gag cgc acc agg gag ctc atc gag cag acc aag cgc      265
Gln Gln Ile Glu Glu Arg Thr Arg Glu Leu Ile Glu Gln Thr Lys Arg
            35                  40                  45 gtg tat gac cag gtt ggc acc cag gag ttt gag gac gtg tcc tac gag      313
Val Tyr Asp Gln Val Gly Thr Gln Glu Phe Glu Asp Val Ser Tyr Glu
        50                  55                  60 agc acg ctc aag gcg ctg gcc gat gtg gag gtc acc tac aca gtt cag      361
Ser Thr Leu Lys Ala Leu Ala Asp Val Glu Val Thr Tyr Thr Val Gln
                65                  70                  75 agg aat atc ctt gac ttc ccc cag cat gtt tcc ccc tcc aag gac atc      409
Arg Asn Ile Leu Asp Phe Pro Gln His Val Ser Pro Ser Lys Asp Ile
 80                  85                  90 cgg aca gcc agc aca gag gcc gac aag aag ctc tct gag ttc gac gtg      457
Arg Thr Ala Ser Thr Glu Ala Asp Lys Lys Leu Ser Glu Phe Asp Val
 95                 100                 105                 110 gag atg agc atg agg gag gac gtg tac cag agg atc gtg tgg ctc cag      505
Glu Met Ser Met Arg Glu Asp Val Tyr Gln Arg Ile Val Trp Leu Gln
                115                 120                 125 gag aaa gtt cag aag gac tca ctg agg ccc gag gct gcg cgg tac ctg      553
Glu Lys Val Gln Lys Asp Ser Leu Arg Pro Glu Ala Ala Arg Tyr Leu
            130                 135                 140 gag cgg cta atc aag ctg ggc cgg aga aat ggg ctt cac ctc ccc aga      601
Glu Arg Leu Ile Lys Leu Gly Arg Arg Asn Gly Leu His Leu Pro Arg
        145                 150                 155 gag act cag gaa aac atc aaa cgc atc aag aag aag ctg agc ctt ctg      649
Glu Thr Gln Glu Asn Ile Lys Arg Ile Lys Lys Lys Leu Ser Leu Leu
    160                 165                 170 tgc atc gac ttc aac aag aac ctg aac gag gac acg acc ttc ctg ccc      697
Cys Ile Asp Phe Asn Lys Asn Leu Asn Glu Asp Thr Thr Phe Leu Pro
175                 180                 185                 190 ttc acg ctc cag gag cta gga ggg ctc ccc gag gac ttt ctg aac tcc      745
Phe Thr Leu Gln Glu Leu Gly Gly Leu Pro Glu Asp Phe Leu Asn Ser
                195                 200                 205 ctg gag aag atg gag gac ggc aag ttg aag gtc acc ctc aag tac ccc      793
Leu Glu Lys Met Glu Asp Gly Lys Leu Lys Val Thr Leu Lys Tyr Pro
            210                 215                 220 cat tac ttc ccc ctc ctg aag aaa tgc cac gtg cct gag acc agg agg      841
His Tyr Phe Pro Leu Leu Lys Lys Cys His Val Pro Glu Thr Arg Arg
        225                 230                 235 aaa gtg gag gag gcc ttc aac tgc cgg tgc aag gag gag aac tgc gct      889
Lys Val Glu Glu Ala Phe Asn Cys Arg Cys Lys Glu Glu Asn Cys Ala
    240                 245                 250 atc ctc aag gag ctg gtg acg ctg cgg gcc cag aag tcc cgc ctg ctg      937
Ile Leu Lys Glu Leu Val Thr Leu Arg Ala Gln Lys Ser Arg Leu Leu
255                 260                 265                 270 ggg ttc cac acg cac gcc gac tat gtc ctg gag atg aac atg gcc aag      985
Gly Phe His Thr His Ala Asp Tyr Val Leu Glu Met Asn Met Ala Lys
                275                 280                 285 acc agc cag acc gtg gcc acc ttc cta gat gag ctg gcg cag aag ctg     1033
Thr Ser Gln Thr Val Ala Thr Phe Leu Asp Glu Leu Ala Gln Lys Leu
            290                 295                 300 aag ccc ctg ggg gag cag gag cgt gcg gtg att ctg gag ctg aag cgt     1081
Lys Pro Leu Gly Glu Gln Glu Arg Ala Val Ile Leu Glu Leu Lys Arg
        305                 310                 315 gcg gag tgc gag cgc cgg ggc ctg ccc ttc gac ggc cgc atc cgt gcc     1129
Ala Glu Cys Glu Arg Arg Gly Leu Pro Phe Asp Gly Arg Ile Arg Ala
    320                 325                 330
```

```
tgg gac atg cgc tac tac atg aac cag gtg gag gag acg cgc tac tgc    1177
Trp Asp Met Arg Tyr Tyr Met Asn Gln Val Glu Glu Thr Arg Tyr Cys
335                 340                 345                 350 gtg gac cag aac ctg ctc aag gag tac ttc ccc gtg cag gtg gtc acg    1225
Val Asp Gln Asn Leu Leu Lys Glu Tyr Phe Pro Val Gln Val Val Thr
                355                 360                 365 cac ggg ctg ctg ggc atc tac cag gag ctc ctg ggg ctg gcc ttc cac    1273
His Gly Leu Leu Gly Ile Tyr Gln Glu Leu Leu Gly Leu Ala Phe His
        370                 375                 380 cac gag gag ggc gcc agt gcc tgg cat gag gac gtg cgg ctc tac acc    1321
His Glu Glu Gly Ala Ser Ala Trp His Glu Asp Val Arg Leu Tyr Thr
    385                 390                 395 gcg agg gac gcg gcc tcg ggg gag gtg gtc ggc aag ttc tac ctg gac    1369
Ala Arg Asp Ala Ala Ser Gly Glu Val Val Gly Lys Phe Tyr Leu Asp
400                 405                 410 ctg tac ccg cgg gaa gga aag tac ggg cac gcg gcc tgc ttt ggc ctg    1417
Leu Tyr Pro Arg Glu Gly Lys Tyr Gly His Ala Ala Cys Phe Gly Leu
415                 420                 425                 430 cag ccc ggc tgc ctg cgg cag gat ggg agc cgc cag atc gcc atc gcg    1465
Gln Pro Gly Cys Leu Arg Gln Asp Gly Ser Arg Gln Ile Ala Ile Ala
                435                 440                 445 gcc atg gtg gcc aac ttc acc aag ccc aca gcc gac gcg ccc tcg ctg    1513
Ala Met Val Ala Asn Phe Thr Lys Pro Thr Ala Asp Ala Pro Ser Leu
        450                 455                 460 ctg cag cat gac gag gtg gag acc tac ttc cat gag ttt ggc cac gtg    1561
Leu Gln His Asp Glu Val Glu Thr Tyr Phe His Glu Phe Gly His Val
    465                 470                 475 atg cac cag ctc tgc tcc cag gcg gag ttc gcc atg ttc agc ggg acc    1609
Met His Gln Leu Cys Ser Gln Ala Glu Phe Ala Met Phe Ser Gly Thr
480                 485                 490 cac gtg gag cgg gac ttt gtg gag gcg ccg tcg cag atg ctg gag aac    1657
His Val Glu Arg Asp Phe Val Glu Ala Pro Ser Gln Met Leu Glu Asn
495                 500                 505                 510 tgg gtg tgg gag cag gag ccg ctg ctg cgg atg tcg cgg cac tac cgc    1705
Trp Val Trp Glu Gln Glu Pro Leu Leu Arg Met Ser Arg His Tyr Arg
                515                 520                 525 aca ggc agc gcc gtg ccc cgg gag ctc ctg gag aag ctc att gag tcc    1753
Thr Gly Ser Ala Val Pro Arg Glu Leu Leu Glu Lys Leu Ile Glu Ser
        530                 535                 540 cgg cag gcc aac aca ggc ctc ttc aac ctg cgc cag atc gtc ctc gcc    1801
Arg Gln Ala Asn Thr Gly Leu Phe Asn Leu Arg Gln Ile Val Leu Ala
    545                 550                 555 aag gtg gac cag gcc ctg cac acg cag acg gac gca gac ccc gcc gag    1849
Lys Val Asp Gln Ala Leu His Thr Gln Thr Asp Ala Asp Pro Ala Glu
560                 565                 570 gag tat gcg cgg ctc tgc cag gag atc ctc ggg gtc ccg gcc acg cca    1897
Glu Tyr Ala Arg Leu Cys Gln Glu Ile Leu Gly Val Pro Ala Thr Pro
575                 580                 585                 590 gga acc aac atg cct gca acc ttc ggc cat ctg gca ggt ggc tac gac    1945
Gly Thr Asn Met Pro Ala Thr Phe Gly His Leu Ala Gly Gly Tyr Asp
                595                 600                 605 gcc cag tac tac ggg tac ctg tgg agc gag gtg tat tcc atg gac atg    1993
Ala Gln Tyr Tyr Gly Tyr Leu Trp Ser Glu Val Tyr Ser Met Asp Met
        610                 615                 620 ttc cac acg cgc ttc aag cag gag ggt gtc ctg aac agc aag gtt ggc    2041
Phe His Thr Arg Phe Lys Gln Glu Gly Val Leu Asn Ser Lys Val Gly
    625                 630                 635
```

-continued

```
atg gat tac aga agc tgc atc ctg aga ccc ggc ggt tcc gag gat gcc    2089
Met Asp Tyr Arg Ser Cys Ile Leu Arg Pro Gly Gly Ser Glu Asp Ala
    640                 645                 650 agc gcc atg ctg agg cgc ttc ctg ggc cgt gac ccc aag cag gac gcc    2137
Ser Ala Met Leu Arg Arg Phe Leu Gly Arg Asp Pro Lys Gln Asp Ala
655             660                 665                 670 ttc ctc ctg agc aag ggg ctg cag gtc ggg ggc tgc gag ccc gag ccg    2185
Phe Leu Leu Ser Lys Gly Leu Gln Val Gly Gly Cys Glu Pro Glu Pro
                675                 680                 685 cag gtc tgc tga ggcctggcac tgcgactgcc cagtctggcc tgcgctcccg        2237
Gln Val Cys * ccgccctggt gccttagccc ccggcacagg atggggcaag ctctggcaca gtgccttggg  2297
actggactgg cagggtggct gagcggctgt cttgcctctt gtcattgtct gtccccaccc  2357
ggtcgtggcc cacccggcta gacggcgtcc tcaaggcatc tggagggctt tcgtggctgc  2417
cagggcctgg tctttgttgc actaacacgt ctcctctctg ggaaacgtcc cttgtcagga  2477
gacggctctt ctttgaaatg aggtcattaa aaggaaac                          2515
```

What is claimed is:

1. A method for identifying a candidate compound capable of treating a hematological disorder, comprising:
   i) combining a compound to be tested with a sample comprising a polypeptide selected from the group consisting of:
      a) a polypeptide comprising the amino acid sequence of SEQ ID NO:2; and
      b) a polypeptide encoded by the nucleotide sequence set forth in SEQ ID NO:1 or SEQ ID NO:3;
   under conditions suitable for binding of the test compound to the polypeptide;
   ii) detecting binding of the test compound to the polypeptide to thereby identify a compound which binds to the polypeptide;
   iii) combining the compound selected in part ii) with primitive erythroid cells expressing the polypeptide; and
   iv) determining if the primitive erythroid cells differentiate into mature cells of the erythroid lineage;
thereby identifying a compound capable of treating a hematological disorder.

2. The method of claim 1, wherein the compound is a small molecule.

3. The method of claim 1, wherein the hematological disorder is anemia.

4. The method of claim 1, wherein the polypeptide further comprises heterologous sequences.

5. The method of claim 1, wherein the binding of the test compound to the polypeptide is detected by a method selected from the group consisting of:
   a) a competition binding assay;
   b) an immunoassay; and
   c) a yeast two-hybrid assay.

6. The method of claim 1, wherein the binding of the test compound to the polypeptide is detected is by an assay for an activity of the polypeptide.

7. The method of claim 6, wherein the assay for activity is a peptidase assay.

8. A method for identifying a candidate compound capable of modulating erythropoeisis comprising:
   i) combining a compound to be tested with a sample comprising a polypeptide selected from the group consisting of:
      a) a polypeptide comprising the amino acid sequence of SEQ ID NO:2; and
      b) a polypeptide encoded by the nucleotide sequence set forth in SEQ ID NO:1 or SEQ ID NO:3;
   under conditions suitable for binding of the test compound to the polypeptide;
   ii) detecting binding of the test compound to the polypeptide to thereby identify a compound which binds to the polypeptide;
   iii) combining the compound selected in part ii) with primitive erythroid cells expressing the polypeptide; and
   iv) determining if the primitive erythroid cells differentiate into mature cells of the erythroid lineage;
thereby identifying a compound capable of modulating erythropoeisis.

9. The method of claim 8, wherein the compound is a small molecule.

10. The method of claim 8, wherein the polypeptide further comprises heterologous sequences.

11. The method of claim 8, wherein the binding of the test compound to the polypeptide is detected by a method selected from the group consisting of:
   a) a competition binding assay;
   b) an immunoassay; and
   c) a yeast two-hybrid assay.

12. The method of claim 8, wherein the binding of the test compound to the polypeptide is detected is by an assay for an activity of the polypeptide.

13. The method of claim 12, wherein the assay for activity is a peptidase assay.

14. The method of claim 1, wherein the sample is selected from the group consisting of an isolated polypeptide or a cell expressing the polypeptide.

15. The method of claim 8, wherein the sample is selected from the group consisting of an isolated polypeptide or a cell expressing the polypeptide.

* * * * *